US011439248B2

(12) United States Patent
Duncan et al.

(10) Patent No.: US 11,439,248 B2
(45) Date of Patent: Sep. 13, 2022

(54) ADJUSTABLE SLEEPING SYSTEM WITH MASSAGE FUNCTION

(71) Applicant: SLEEP TECHNOLOGIES, LLC, Harlingen, TX (US)

(72) Inventors: Robert B Duncan, Harlingen, TX (US); Matthew Hayward, Richardson, TX (US); Heather D. Benoit, Austin, TX (US); Mark W. Foohey, Austin, TX (US); J. Kevin Gentry, Austin, TX (US)

(73) Assignee: SLEEP TECHNOLOGIES, LLC, Harlingen, TX (US)

( * ) Notice: Subject to any disclaimer, the term of this patent is extended or adjusted under 35 U.S.C. 154(b) by 160 days.

(21) Appl. No.: 16/713,759

(22) Filed: Dec. 13, 2019

(65) Prior Publication Data

US 2020/0188222 A1    Jun. 18, 2020

Related U.S. Application Data

(60) Provisional application No. 62/779,629, filed on Dec. 14, 2018.

(51) Int. Cl.
*A47C 27/06*    (2006.01)
*A47C 27/045*   (2006.01)
(Continued)

(52) U.S. Cl.
CPC .......... *A47C 27/061* (2013.01); *A47C 23/002* (2013.01); *A47C 27/045* (2013.01);
(Continued)

(58) Field of Classification Search
CPC ................ A47C 23/00; A47C 23/001; A47C 23/04–0438; A47C 27/04–0453;
(Continued)

(56) References Cited

U.S. PATENT DOCUMENTS

| 1,276,760 A | 8/1918 | Hines |
| 2,315,706 A | 5/1939 | Hopkes |

(Continued)

FOREIGN PATENT DOCUMENTS

| CA | 1265262 A | 1/1990 |
| CA | 55629 S | 3/1990 |

(Continued)

OTHER PUBLICATIONS

International Searching Authority, Search Report and Written Opinion for related PCT/US2019/066368, dated Apr. 2, 2020; 10 pages.

(Continued)

*Primary Examiner* — Valerie L Woodward
*Assistant Examiner* — Paige Kathleen Bugg
(74) *Attorney, Agent, or Firm* — Dickinson Wright PLLC; Mark E. Scott; Nicholas Martin

(57) ABSTRACT

Adjustable sleeping system with massage function. At least one example embodiment is a method of operating a sleeping system, the method including massaging a person residing on a sleeping surface of the sleeping system, the massaging by driving a plurality of adjustable spring assemblies, the plurality of adjustable spring assemblies part of an array of adjustable spring assemblies arranged such that a top of each adjustable spring assembly defines an upper surface parallel to the sleeping surface.

25 Claims, 16 Drawing Sheets

(51) Int. Cl.
  *A47C 23/00* (2006.01)
  *A47C 31/12* (2006.01)
  *A61H 23/00* (2006.01)
  *A61H 23/02* (2006.01)
  *A47C 23/04* (2006.01)
  *A61B 5/00* (2006.01)

(52) U.S. Cl.
  CPC .......... *A47C 27/065* (2013.01); *A47C 31/123* (2013.01); *A61H 23/004* (2013.01); *A61H 23/0254* (2013.01); *A47C 23/04* (2013.01); *A47C 27/064* (2013.01); *A61B 5/6891* (2013.01); *A61H 2201/5061* (2013.01); *A61H 2203/0443* (2013.01)

(58) Field of Classification Search
  CPC .... A47C 27/05–056; A47C 27/06–065; A47C 27/068; A47C 27/07; A47C 31/123; A61G 7/00–002; A61G 7/015; A61G 7/018
  USPC .......................................................... 601/134
  See application file for complete search history.

(56) References Cited

U.S. PATENT DOCUMENTS

| | | |
|---|---|---|
| 2,558,288 A | 3/1947 | Backus |
| 2,595,072 A | 3/1948 | Gottschalk |
| 2,630,585 A | 7/1950 | Reese |
| 3,656,190 A * | 4/1972 | Regan ............... A47C 23/002 5/613 |
| 4,175,549 A | 11/1979 | Hamer |
| 4,222,137 A | 9/1980 | Usami |
| 4,644,593 A | 2/1987 | O'Brien |
| 4,644,597 A | 2/1987 | Walker |
| 4,766,597 A | 8/1988 | Olshansky |
| 4,766,628 A | 8/1988 | Walker |
| 4,788,729 A | 12/1988 | Walker |
| 4,799,276 A | 1/1989 | Kadish |
| D300,194 S | 3/1989 | Walker |
| 4,890,344 A | 1/1990 | Walker |
| 4,897,890 A | 2/1990 | Walker |
| 4,908,895 A | 3/1990 | Walker |
| 4,991,244 A | 2/1991 | Walker |
| 5,144,706 A | 9/1992 | Walker |
| 5,170,522 A | 12/1992 | Walker |
| 5,170,552 A | 12/1992 | Swiderski et al. |
| 5,305,738 A | 4/1994 | Shimizu |
| 5,509,154 A | 4/1996 | Shafer et al. |
| 5,523,040 A | 6/1996 | Krouskop |
| 5,542,907 A | 8/1996 | Chou |
| 5,564,140 A | 10/1996 | Shoenhair et al. |
| 5,625,914 A | 5/1997 | Schwab |
| 5,642,546 A | 7/1997 | Shoenhair |
| 5,904,172 A | 5/1999 | Gifft et al. |
| 6,098,223 A | 8/2000 | Larson |
| 6,146,342 A | 11/2000 | Glen |
| 6,161,231 A | 12/2000 | Kraft et al. |
| 6,202,239 B1 | 3/2001 | Ward et al. |
| 6,397,419 B1 | 6/2002 | Mechache |
| 6,487,738 B1 | 12/2002 | Graebe |
| 6,560,804 B2 | 5/2003 | Wise et al. |
| 6,686,711 B2 | 2/2004 | Rose et al. |
| 6,708,357 B2 | 3/2004 | Gaboury et al. |
| 6,721,981 B1 | 4/2004 | Greenhalgh |
| 6,763,541 B2 | 7/2004 | Mahoney et al. |
| 6,804,848 B1 | 10/2004 | Rose |
| 6,832,397 B2 | 12/2004 | Gaboury et al. |
| 6,883,191 B2 | 4/2005 | Gaboury et al. |
| 7,069,610 B1 | 7/2006 | Chai |
| 7,107,642 B2 | 9/2006 | Wong et al. |
| 7,270,222 B1 | 9/2007 | Aymar |
| 7,676,872 B2 | 3/2010 | Block |
| 7,856,895 B2 | 12/2010 | Syassen |
| 7,865,988 B2 | 1/2011 | Koughan et al. |
| 7,934,277 B1 | 5/2011 | Shu |
| 7,941,882 B1 | 5/2011 | Strozer |
| 8,328,287 B2 | 12/2012 | Hsu |
| 8,341,786 B2 | 1/2013 | Oexman et al. |
| D698,338 S | 1/2014 | Ingham et al. |
| 8,672,842 B2 | 3/2014 | Kenalty et al. |
| 8,672,853 B2 | 3/2014 | Young |
| 8,752,222 B2 | 6/2014 | Papaioannou |
| 8,769,747 B2 | 7/2014 | Mahoney et al. |
| 8,844,079 B2 | 9/2014 | Skinner et al. |
| 8,844,943 B2 | 9/2014 | Kim |
| 8,973,183 B1 | 3/2015 | Palashewski et al. |
| 9,131,782 B1 | 9/2015 | Baker |
| 9,138,065 B2 | 9/2015 | Chandler |
| 9,836,930 B2 | 12/2017 | De Luca |
| 9,924,813 B1 | 3/2018 | Basten et al. |
| 9,933,775 B2 | 4/2018 | Saavedra |
| 9,955,795 B2 | 5/2018 | Krenik |
| 10,010,187 B1 | 7/2018 | Mencia |
| 10,334,957 B2 | 7/2019 | Edling |
| 10,416,031 B2 | 9/2019 | Hsu et al. |
| 10,561,253 B2 | 2/2020 | Tsern et al. |
| 11,021,029 B2 | 6/2021 | Harrison |
| 2002/0184711 A1 | 12/2002 | Mahoney et al. |
| 2004/0231057 A1 | 11/2004 | Sabin |
| 2005/0204475 A1 | 9/2005 | Schmitz et al. |
| 2005/0235417 A1 | 10/2005 | Koughan et al. |
| 2005/0257883 A1 | 11/2005 | Anagnostopoulos |
| 2006/0253994 A1 | 11/2006 | Sprinks et al. |
| 2008/0035156 A1 | 2/2008 | Hyde et al. |
| 2008/0052830 A1 | 3/2008 | Koughan et al. |
| 2008/0077020 A1 | 3/2008 | Young et al. |
| 2008/0052837 A1 | 5/2008 | Blumberg |
| 2008/0276377 A1 | 11/2008 | Hsu |
| 2009/0038080 A1 | 2/2009 | Grigg |
| 2010/0043148 A1 | 2/2010 | Rose et al. |
| 2010/0170043 A1 | 7/2010 | Young et al. |
| 2010/0174198 A1 | 7/2010 | Young et al. |
| 2010/0174199 A1 | 7/2010 | Young et al. |
| 2010/0218315 A1 | 9/2010 | Hyde et al. |
| 2010/0257675 A1* | 10/2010 | DeMoss ............... A47C 27/065 5/720 |
| 2010/0325810 A1 | 12/2010 | Dahlin et al. |
| 2011/0010014 A1 | 1/2011 | Oexman et al. |
| 2011/0144455 A1 | 6/2011 | Young et al. |
| 2011/0296621 A1 | 12/2011 | McKenna |
| 2011/0296622 A1 | 12/2011 | Hsu |
| 2011/0314612 A1 | 12/2011 | Hsu |
| 2012/0042454 A1 | 2/2012 | Viberg |
| 2012/0056458 A1 | 3/2012 | Hsu |
| 2012/0110744 A1 | 5/2012 | Hsu |
| 2012/0186019 A1 | 7/2012 | Rawls-Meehan |
| 2013/0000049 A1 | 1/2013 | Hsu |
| 2013/0089717 A1 | 4/2013 | Loffelmann et al. |
| 2013/0283530 A1* | 10/2013 | Main ............... A47C 27/083 5/600 |
| 2013/0340175 A1 | 12/2013 | Stevens et al. |
| 2014/0007656 A1 | 1/2014 | Mahoney |
| 2014/0059775 A1* | 3/2014 | Khanzadian ......... B29C 39/003 5/655.5 |
| 2014/0114486 A1 | 4/2014 | Ponnuhamy |
| 2014/0137332 A1 | 5/2014 | McGuire et al. |
| 2014/0137337 A1* | 5/2014 | DeFranks ............ A47C 27/14 5/723 |
| 2014/0182061 A1 | 7/2014 | Zaiss et al. |
| 2014/0250597 A1 | 9/2014 | Chen et al. |
| 2014/0257571 A1 | 9/2014 | Chen et al. |
| 2014/0259417 A1 | 9/2014 | Nunn et al. |
| 2014/0259418 A1 | 9/2014 | Nunn et al. |
| 2014/0259419 A1 | 9/2014 | Stusynski et al. |
| 2014/0259431 A1 | 9/2014 | Fleury et al. |
| 2014/0259433 A1 | 9/2014 | Nunn et al. |
| 2014/0259434 A1 | 9/2014 | Nunn et al. |
| 2014/0277611 A1 | 9/2014 | Nunn et al. |
| 2014/0277778 A1 | 9/2014 | Nunn et al. |
| 2014/0277822 A1 | 9/2014 | Nunn et al. |
| 2015/0007393 A1 | 1/2015 | Palashewski |
| 2015/0008710 A1 | 1/2015 | Young et al. |

(56) References Cited

U.S. PATENT DOCUMENTS

| | | |
|---|---|---|
| 2015/0025327 A1 | 1/2015 | Young et al. |
| 2015/0108188 A1 | 4/2015 | MacLachlan et al. |
| 2015/0182033 A1 | 7/2015 | Brosnan et al. |
| 2015/0182397 A1 | 7/2015 | Palashewski et al. |
| 2015/0182399 A1 | 7/2015 | Rose et al. |
| 2015/0182418 A1 | 7/2015 | Zaiss |
| 2015/0290059 A1 | 10/2015 | Brosnan et al. |
| 2015/0351982 A1 | 12/2015 | Krenik |
| 2016/0015184 A1 | 1/2016 | Nunn et al. |
| 2016/0058641 A1 | 3/2016 | Moutafis et al. |
| 2016/0073789 A1 | 3/2016 | Hyltenfeldt et al. |
| 2016/0100696 A1 | 4/2016 | Palashewski et al. |
| 2016/0192886 A1 | 7/2016 | Nunn et al. |
| 2016/0242562 A1 | 8/2016 | Karschnik et al. |
| 2016/0367039 A1 | 12/2016 | Young et al. |
| 2017/0000685 A1* | 1/2017 | Rohr .............. A47C 27/082 |
| 2017/0003666 A1 | 1/2017 | Nunn et al. |
| 2017/0035212 A1 | 2/2017 | Erko et al. |
| 2017/0049243 A1 | 2/2017 | Nunn et al. |
| 2017/0065220 A1 | 3/2017 | Young et al. |
| 2017/0128297 A1 | 5/2017 | Cernasov et al. |
| 2017/0173262 A1 | 6/2017 | Veltz |
| 2017/0191516 A1 | 7/2017 | Griffith et al. |
| 2017/0208941 A1 | 7/2017 | Trakic |
| 2017/0224124 A1* | 8/2017 | Blumberg ............ A47C 27/083 |
| 2017/0303697 A1 | 10/2017 | Chen et al. |
| 2017/0312155 A1 | 11/2017 | Copetti |
| 2017/0354268 A1 | 12/2017 | Brosnan et al. |
| 2017/0356815 A1 | 12/2017 | Madden et al. |
| 2018/0036198 A1* | 2/2018 | Mergl .................. A61H 23/02 |
| 2018/0192781 A1 | 7/2018 | Hyltenfeldt et al. |
| 2018/0199726 A1 | 7/2018 | Greenhalgh et al. |

FOREIGN PATENT DOCUMENTS

| | | |
|---|---|---|
| CA | 1281820 C | 3/1991 |
| CA | 77379 S | 10/1995 |
| CN | 204306471 U | 5/2015 |
| EP | 2893847 A1 | 7/2015 |
| EP | 3034060 A1 * | 6/2016 |
| NL | 1035506 C2 | 12/2009 |
| WO | 0002516 A1 | 1/2000 |
| WO | 2007070397 A2 | 6/2007 |
| WO | 2016138082 A1 | 9/2016 |

OTHER PUBLICATIONS

International Searching Authority, Search Report and Written Opinion for related PCT/US2019/066380, dated Feb. 19, 2020; 8 pages.

International Searching Authority, Search Report and Written Opinion for related PCT/US2019/066348, dated Feb. 21, 2020; 10 pages.

International Searching Authority, Search Report and Written Opinion for related PCT/US2019/066362, dated Feb. 20, 2020; 8 pages.

Excel Medical Supplies, "Alternating Pressure and Continuous Low Air Loss Relief", Published Apr. 1, 2014; Retrieved from Internet on May 26, 2016; 1 page.

Muscular Dystrophy Association, "One Good Turn", Published Aug. 31, 2006; <https://www.mda.org/quest/article/one-good-turn>, Retrieved from the Internet on Dec. 13, 2019; 10 pages.

Smart Mattress Company BV, "Smart Mattress"; <http://www.smartmattress.nl/?lang-en>, Retrieved from the Internet on Dec. 13, 2019; 1 page.

* cited by examiner

US 11,439,248 B2

ADJUSTABLE SLEEPING SYSTEM WITH MASSAGE FUNCTION

CROSS-REFERENCE TO RELATED APPLICATIONS

This application claims the benefit of provisional application Ser. No. 62/779,629, filed Dec. 14, 2018, titled "Adjustable Sleeping System", and the provisional application is incorporated by reference herein as if reproduced in full below.

BACKGROUND

Getting a good night's sleep is important. Some studies suggest that lack of sleep, or lack of sufficiently restful sleep, has long term health consequences. The long term health consequences include increased risk of dementia and Alzheimer's disease. Some factors that adversely affect the ability to get a good night's sleep are physiological, such as snoring, central apnea, obstructive apnea, and restless leg syndrome. However, other factors are environmental, such as the compliance of the sleep surface upon which sleep is attempted, and sleeping position (though some physiological factors are sleep position dependent).

Many mattresses and beds purport to increase the restfulness of sleep. For example, one attempt in recent years is based on mattresses made of combinations of closed- and open-cell foams that purport to reduce high force areas regardless of sleep position, and to reduce communication of movement to sleeping partners. Other attempts in recent years use air bladders to create individual pockets of support, usually in horizontal rows across the width of a mattress. The air bladder mattresses enable changing air pressure within the bladders, and thus changing the force carried by each bladder. Each system has its respective drawbacks.

Any system and/or method which increases user comfort and flexibility of control would provide a competitive advantage in the marketplace.

BRIEF DESCRIPTION OF THE DRAWINGS

For a detailed description of example embodiments, reference will now be made to the accompanying drawings in which.

DEFINITIONS

Figure 1:
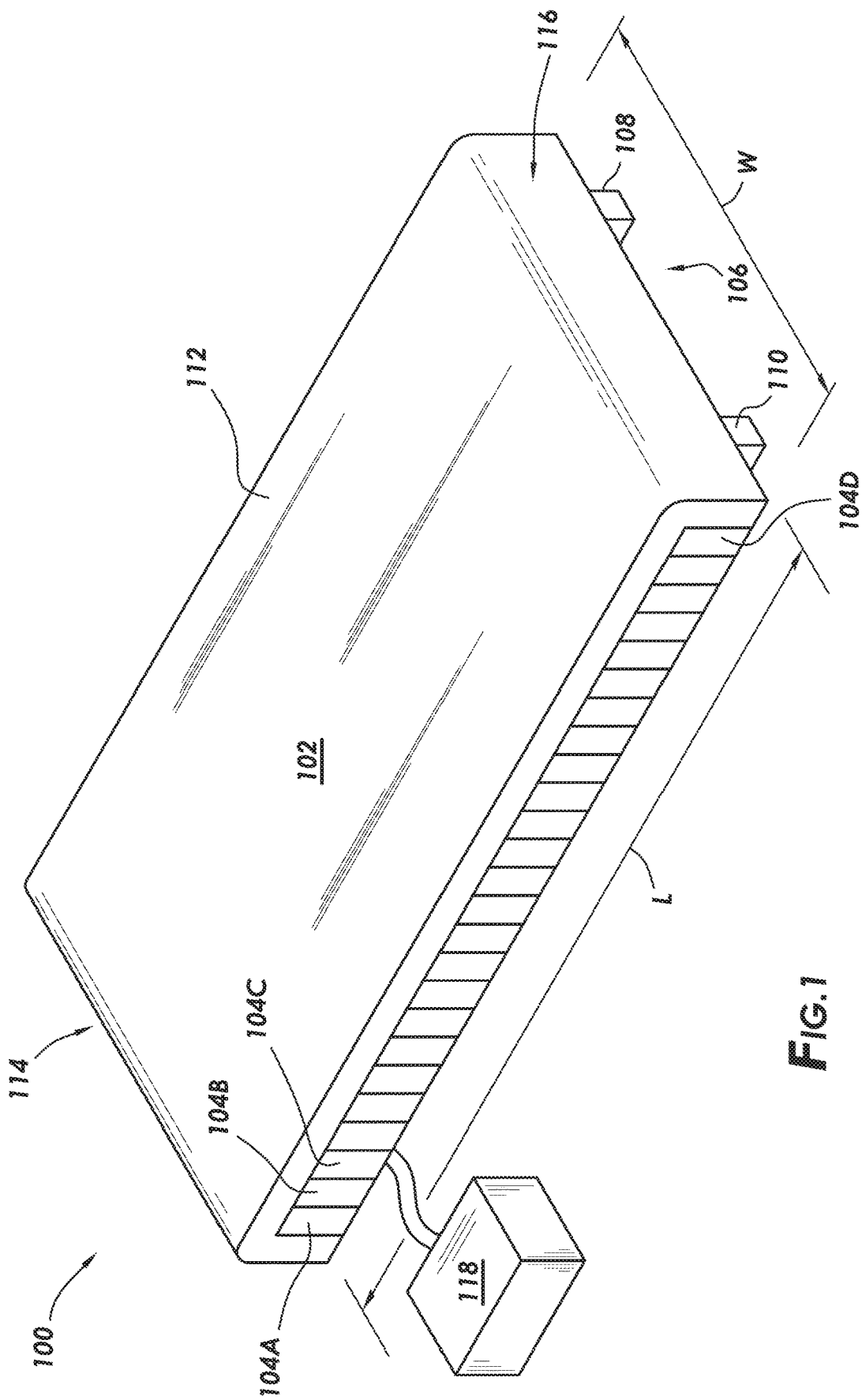
FIG. 1 shows a perspective view of an adjustable sleeping system in accordance with at least some embodiments.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . " Also, the term "couple" or "couples" is intended to mean either an indirect or direct connection. Thus, if a first device couples to a second device, that connection may be through a direct connection or through an indirect connection via other devices and connections.

"About" in reference to a numerical value shall mean the numerical value plus or minus 20 percent (+/−20%).

"Controller" shall mean, alone or in combination, individual circuit components, an application specific integrated circuit (ASIC), a microcontroller with controlling software, a digital signal processor (DSP), a processor with controlling software, or a field programmable gate array (FPGA), configured to read inputs and drive outputs responsive to the inputs.

"Random" shall mean in pattern that appears random to an ordinary observer, and shall include pseudo-random sequences created by algorithms.

"Un-laden compression" shall refer to an amount a spring is compressed in the absence of a person or other object residing on a sleeping surface of the bed. Having an un-laden compression shall not obviate the fact that compression may be adjustable when the spring is carrying or supporting an external weight or force.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Various embodiments are directed to an adjustable sleeping system comprising an array of adjustable spring assemblies. Each adjustable spring assembly is adjustable by a bed controller to implement control of force distribution. Having individually adjustable spring assemblies enables a host of operational modes and methods. For example, the control of force distribution may enable functions such as overall control of firmness across the adjustable sleeping system and to area-specific functions. Area-specific functions may include a massage function, force equalization within the area of the person's body to reduce pressure points, disembarkation assistance, and encouraging a roll to reduce sleep issues (e.g., snoring), to name a few. The specification first turns to a high level overview of the adjustable sleeping system in accordance with example embodiments.

FIG. 1 shows a perspective view of an adjustable sleeping system 100 in accordance with at least some embodiments. In particular, the example adjustable sleeping system 100 defines a length L, a width W, and a sleeping surface 102. The length L and width W may be any suitable size, such as a cot size, a single size, a twin size, a twin XL size, a full size, a Queen size, a "California" King, King size, or specialty sizes (e.g., for boats, motor homes, travel trailers). In some cases, the overall bed may comprise two adjustable sleeping systems 100 arranged side-by-side (e.g., two twin XL size beds side-by-side to form a King size). The adjustable sleeping system 100 further comprises a plurality of adjustable spring assemblies 104. FIG. 1 labels only four of the visible adjustable spring assemblies 104 (104A-104D) so as not to unduly complicate the figure. The adjustable spring assemblies are modular components that may be placed at any location, and thus a single adjustable spring assembly will be referred to as an "adjustable spring assembly 104" and groups of adjustable spring assemblies will be referred to as "adjustable spring assemblies 104." The adjustable spring assemblies 104 are discussed in more detail below. In example systems, the adjustable spring assemblies 104 are mechanically coupled to a bed frame 106 comprising a first frame rail 108 and a second frame rail 110.

An upper surface of the adjustable spring assemblies 104 (the upper surface not visible in FIG. 1) is covered with a topper or overlay 112, such as open-cell or closed-cell foam. In one example embodiment the overlay 112 comprises a foam padding having a thickness of three inches (measured perpendicularly to the sleeping surface 102). Other thicknesses, both greater and smaller, and other constituent materials, may be used. The example overlay 112 wraps around the head end 114 of the adjustable sleeping system 100, and also wraps around the foot end 116 of the adjustable sleeping system 100. In other cases, the wrapping aspects of the overlay 112 may be omitted, and the adjustable spring assemblies 104 on the head end 114 will be exposed on the head end 114, and the adjustable spring assemblies 104 on the foot end 116 will be exposed on the foot end 116. In yet still other cases, the overlay 112 may be omitted entirely. In such situations, an upper surface defined by each adjustable spring assembly 104 may define the sleeping surface 102.

The adjustable sleeping system 100 further comprises a bed controller 118 communicatively and controllably coupled to each adjustable spring assembly 104. The bed controller 118 is configured to selectively control a weight or force carried by each adjustable spring assembly 104 to control force distribution among the adjustable spring assemblies 104. The bed controller 118 may take any suitable form. An example bed controller 118 is discussed below in reference to FIG. 8.

Figure 2:
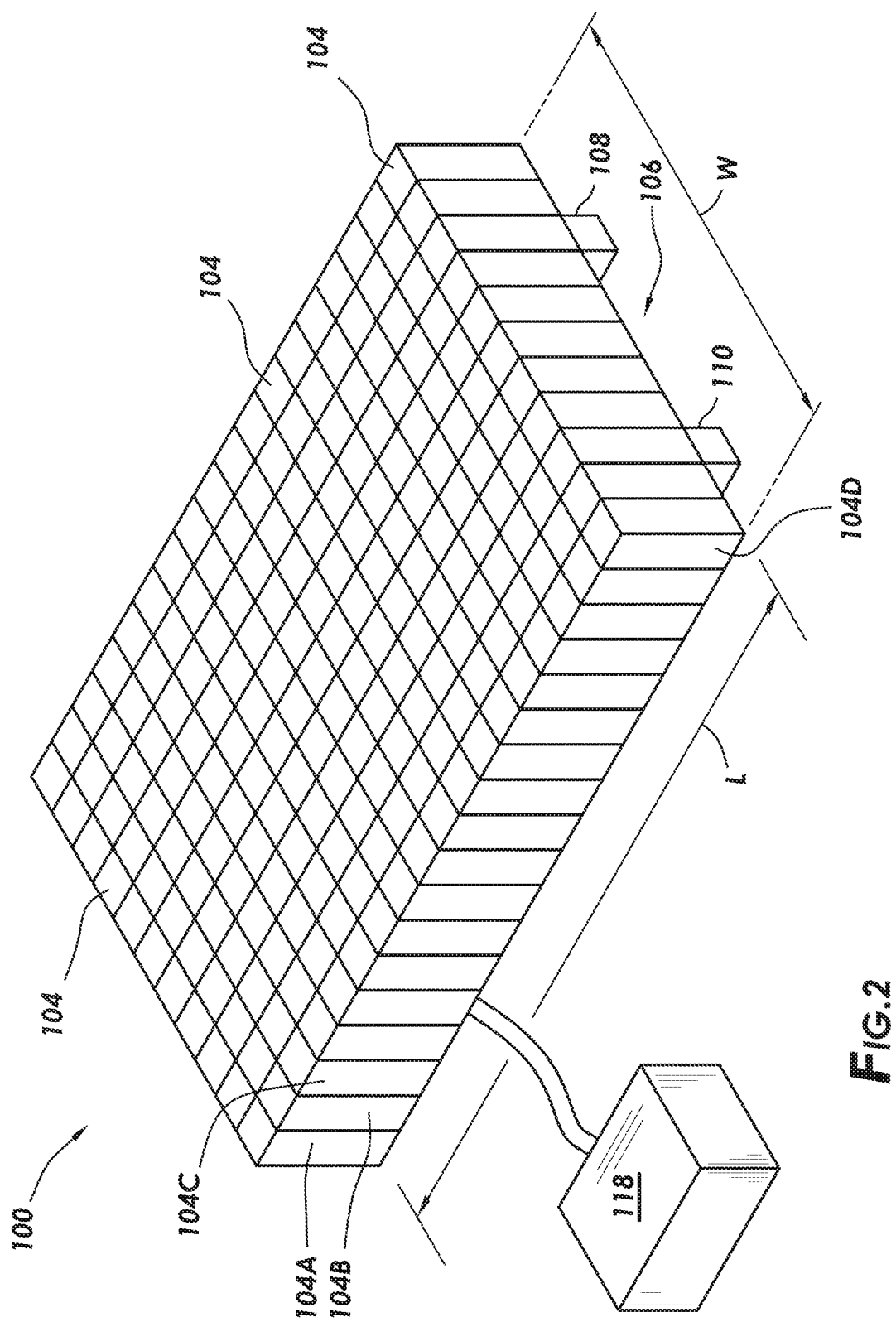
FIG. 2 shows a perspective view of an adjustable sleeping system with the overlay removed, and in accordance with at least some embodiments.

FIG. 2 shows a perspective view of the adjustable sleeping system 100 with the overlay 112 removed, and in accordance with at least some embodiments. In particular, the example adjustable sleeping system 100 comprises a matrix or array of adjustable spring assemblies 104 mechanically coupled to the bed frame 106. The array of adjustable spring assemblies 104 is arranged such that a top of each adjustable spring assembly 104 defines an upper surface parallel to the sleeping surface 102 (FIG. 1). The example array is a grid pattern, where the adjustable spring assemblies 104 in a row (i.e., parallel to the width W) are aligned, and the adjustable spring assemblies 104 in a column (i.e., parallel to the length L) are aligned. However, other arrangements of the array are possible, such as a honeycomb pattern.

In the example case of a twin size bed, between 8 and 40 adjustable spring assemblies 104 reside in each row, in one example case between 10 and 15 adjustable spring assemblies 104, and in a particular case 13 adjustable spring assemblies 104 reside in each row. Moreover, in an example twin sized bed, between 15 and 80 adjustable spring assemblies 104 may reside in each column, in some cases between 20 and 30 adjustable spring assemblies 104, and in some cases 25 adjustable spring assemblies 104 reside in each column. Thus, for a twin size bed, 120 or greater adjustable spring assemblies 104 may be used, in some cases 200 or greater adjustable spring assemblies 104 may be used, and in some cases 250 or greater adjustable spring assemblies 104 may be used. For a King size bed (e.g., two twin XL size beds side-by-side) or a Queen sized bed, 200 or greater adjustable spring assemblies 104 may be used, in some cases 400 or greater adjustable spring assemblies 104 may be used, and in a particular case 500 or greater adjustable spring assemblies 104 may be used. For a cot size bed, 100 or greater adjustable spring assemblies 104 may be used, in some cases 300 or greater adjustable spring assemblies 104 may be used. The size of the adjustable spring assemblies 104, and the spacing between the adjustable spring assemblies 104, affects the number of adjustable spring assemblies 104. Each adjustable spring assembly 104 comprises a spring and an actuator (e.g., a hydraulic cylinder, a bellows, or a motor) such that the force carried by the spring can be adjusted. Example adjustable spring assemblies 104 are discussed next.

Figure 3:
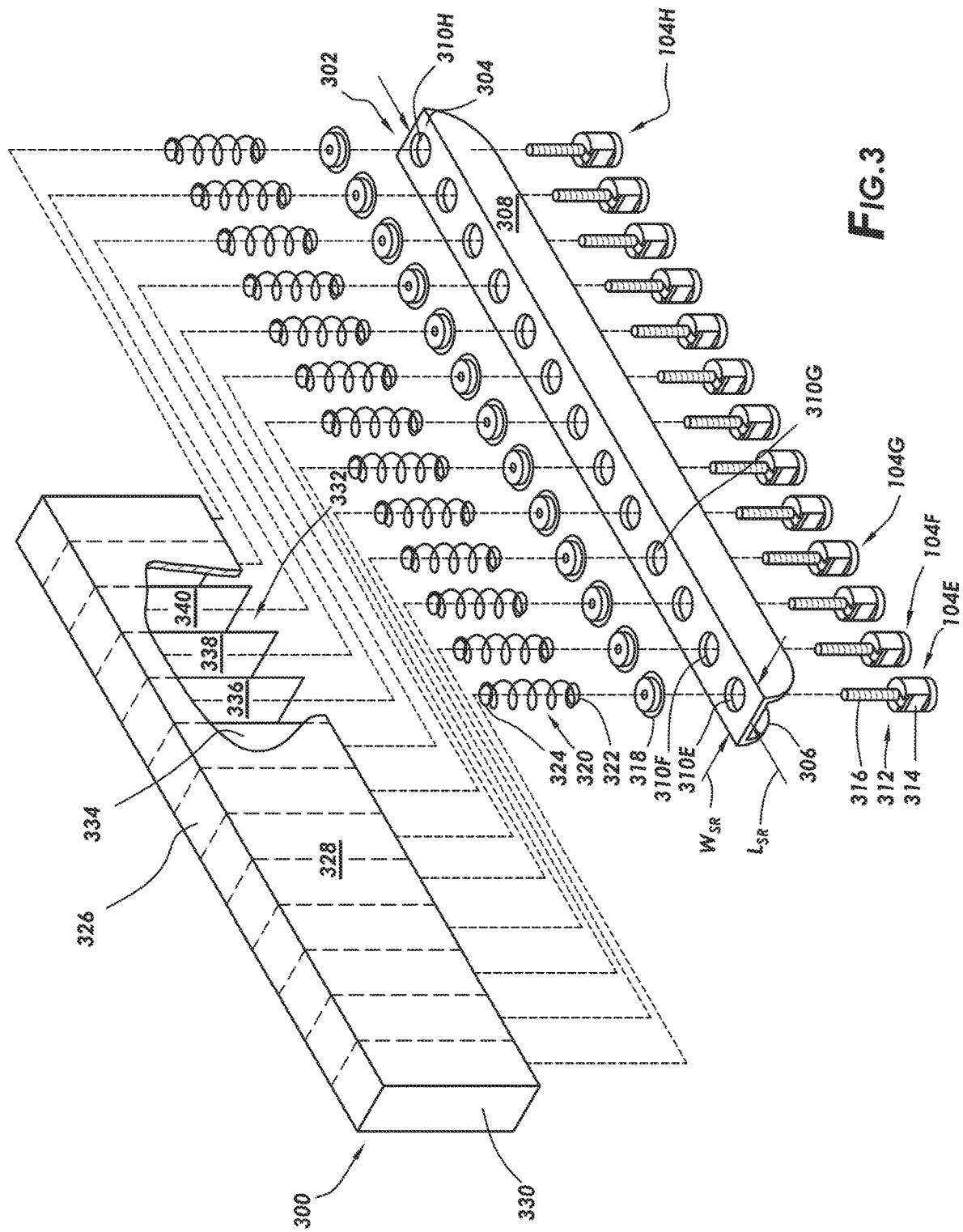
FIG. 3 shows an exploded perspective view of row of adjustable spring assemblies in accordance with at least some embodiments.

FIG. 3 shows an exploded perspective view of row of adjustable spring assemblies in accordance with at least some embodiments. In particular, visible in FIG. 3 are a baffle box 300, a spring rail 302, as well as a plurality of adjustable spring assemblies 104. As noted above, between 8 and 40 adjustable spring assemblies 104 may reside in a row, and in a particular case 13 adjustable spring assemblies 104 reside in a row. FIG. 3 labels only four of the adjustable spring assemblies 104 (104E-104H) so as not to unduly complicate the figure. Again, the adjustable spring assemblies 104 are modular components that may be placed at any location within a row or column. The various example components will be addressed in turn, starting with the spring rail 302.

The example spring rail 302 defines a long dimension or length $L_{SR}$. When assembled into an adjustable sleeping system 100 (FIG. 1), the length $L_{SR}$ is parallel to the width W (FIG. 1) and perpendicular to the length L (FIG. 1) of the adjustable sleeping system 100. In cases where the adjustable sleeping system 100 is a cot width or a twin width, the length $L_{SR}$ will be about same as the width W. In cases where the overall adjustable sleeping system 100 is a Queen size, a "California" King, or a King size, the length $L_{SR}$ may be half the overall width W. The spring rail 302 also defines a width $W_{SR}$. When assembled into an adjustable sleeping system 100, the width $W_{SR}$ is parallel to the length L and perpendicular to the width W of the adjustable sleeping system 100. In example cases the width $W_{SR}$ is between and including 1 inch and 6 inches, and in some cases the width $W_{SR}$ is 3 inches. The example spring rail 302 further comprises an upper surface 304 and a corresponding lower surface (not visible in FIG. 3). Moreover, FIG. 3 shows the example spring rail 302 has two downwardly projecting walls or downwardly projecting legs, including downwardly projecting leg 306 on a first side of the spring rail 302 and running along the length $L_{SR}$, and a downwardly projecting leg 308 on the opposite side of the spring rail 302 and running along the length $L_{SR}$. Further, the example spring rail 302 defines a plurality of apertures 310. The number of apertures 310 may correspond directly to the number of adjustable spring assemblies 104, and thus in some cases between 8 and 40 apertures 310 are present. FIG. 3 labels only four of the apertures 310 (310E-310H) so as not to unduly complicate the figure. Each individual aperture 310 will be referred to as "aperture 310," and groups of apertures will be referred to as "apertures 310." The apertures 310 are spaced along the length $L_{SR}$, and each aperture 310 extends from the upper surface 304 to the lower surface of the spring rail 302. In example embodiments, the spring rail 302 is made of metallic material, but any suitable material (e.g., high strength plastic, fiberglass) may be used.

The discussion now turns to the adjustable spring assemblies 104. Referring to adjustable spring assembly 104E as representative of all the adjustable spring assemblies, the example adjustable spring assembly 104E comprises a motor 312 with a stator 314 and a rotor (the rotor not visible in FIG. 3). The rotor of the motor 312 is coupled to a lead screw 316. The motor 312 may comprise any suitable electric motor that can turn the lead screw 316, such as a stepper motor, a direct current (DC) motor, or an alternating current (AC) motor (e.g., squirrel cage or synchronous). Regardless of the type of motor 312, the motor 312 is controlled by the bed controller 118 (FIG. 1). In one example embodiment, the motor 312 is housed in a National Electrical Manufacturers Association (NEMA) 17 body, but other body types are also contemplated. In example embodiments, the stator 314 is coupled to the spring rail 302 in any suitable fashion.

The lead screw 316 is rigidly coupled to the rotor. Thus, as the rotor of the motor 312 turns, so too does the lead screw 316, but the lead screw 316 does not translate along its longitudinal axis; rather, the orientation and positon of the lead screw 316 relative to the upper surface 304 remains the same. Thus, the lead screw 316 in the example embodiments is referred to as a captive lead screw. However, in other cases the lead screw may be implemented as a non-captive lead screw, where turning of the rotor translates the lead screw along the longitudinal axis of the lead screw.

When assembled, the lead screw 316 extends above the upper surface 304 of the spring rail 302. A spring perch or spring plate 318 is coupled to the lead screw 316 such that as the lead screw 316 is turned by the motor 312, the spring plate 318 translates up and down along the longitudinal central axis of the lead screw 316. In embodiments where the lead screw 316 is a captive lead screw, the axial relationship of the lead screw 316 to the motor 312 does not change, and the spring plate 318 is threadingly coupled to the lead screw 316 such that as the lead screw 316 turns, the axial location of the spring plate 318 along the lead screw 316 changes. The example lead screw 316 may have an 8 millimeter diameter, but larger and smaller diameters are also contemplated.

The representative adjustable spring assembly 104E further comprises a main spring 320 in the form of a coil or helical spring having a first end 322 and a second end 324. When assembled, the first end 322 of the main spring 320 couples to the spring plate 318, and the second end 324 abuts an inside surface of the baffle box 300 of fabric. The example main spring 320 is a helical spring that is "barreled," meaning that the main spring 320 has a larger diameter at its medial portion, and smaller diameters at the first end 322 and second end 324, thus taking the exterior shape of an elongated whiskey barrel. Barreling of the main spring 320 reduces buckling of the main spring under loads tending to torque the main spring 320 across the central axis of the main spring 320. In other cases the main spring 320 may have a single diameter along the entire height. In accordance with at least some embodiments, the main spring 320 has a constant spring factor K along its length. In other cases, however, the main spring 320 may have two or more spring constants along its length. In the example case of two spring constants, the main spring 320 may have a first portion having a first spring constant K1 and a second portion having a second spring constant K2, where the first spring constant K1 is different than the second spring constant K2. Having a main spring with two or more spring constants may enable finer control of the force carried for lighter loads.

Regardless of the exterior shape and/or how many spring constants the main spring 320 may implement, in example embodiments the main spring 320 has a free or un-laden height of between and including 5 inches to 20 inches, in some cases between and including 8 inches to 15 inches, and in a particular case about 11 inches. When the components of FIG. 3 are fully assembled, the baffle box 300 compresses or preloads each main spring 320, making the pre-load height between and including 4 inches to 19 inches, in some cases between and including 7 inches to 14 inches, and in a particular case about 10 inches.

Still referring to FIG. 3, the example system further comprises the baffle box 300. The example baffle box 300 is shown in partial cut-away to highlight some of the interior components. The baffle box 300 defines a top wall 326, a first side wall 328, a second side wall opposite the first side wall 328 (the second side wall not visible in FIG. 3), a first end wall 330, a second end wall opposite the first end wall 330 (the second end wall not visible in FIG. 3), and an interior volume 332. Disposed within the interior volume 332 are a plurality of baffles (e.g., baffles 334, 336, 338, and 340). The locations of the remaining baffles are illustrated by dashed lines along the top wall 326 and first side wall 328. Each baffle extends between the first side wall 328 and the second side wall, and the plurality of baffles thus create or define a plurality of pockets within the baffle box 300. When assembled, each pocket of the baffle box 300 is telescoped over a main spring 320 of a respective adjustable spring assembly 104. In example cases, each pocket of the baffle box 300 is coupled on a lower end directly or indirectly to the spring rail 302. In some cases, each pocket of the baffle box 300 is coupled to a top plate of the motor 312, as will be discussed in greater detail below.

The baffle box 300 in example cases is made of fabric material, and serves several purposes. First, the baffles (e.g., baffles 334, 336, 338, and 340) physically separate the main springs 320 from each other to reduce or eliminate the possibility of the spring coils interfering with each other. Moreover, the baffle box 300 acts to slightly compress and thus preload each main spring 320. Further still, the baffle box 300 physically couples the main springs 320 to each other to provide structural support against forces tending to displace the tops of the main springs 320 away from alignment with the longitudinal central axes of the lead screws 316. In yet still other cases, the baffle box 300 may also act alone or in combination with other components to hold the spring plate 318 against rotation when the motor 312 is turning the lead screw 316 (e.g., by holding the upper ends of the main springs against rotation).

As shown in FIG. 3, in example cases each row (e.g., of a twin size bed)) is created by coupling a plurality of adjustable spring assemblies 104 to a spring rail 302. However, the various embodiments are not limited to that particular construction. For example, a spring rail may define a column rather than a row. Moreover, the spring rail may be omitted and each adjustable spring assembly 104 may couple to a different underlying structure (e.g., twin size metallic plate with apertures therein) that enables the array format of the adjustable spring assemblies. While FIG. 3 shows the use of the baffle box 300 to create the pockets to keep the main springs separated, in other cases each individual adjustable spring assembly 104 may have a dedicated sock of fabric material telescoped over the main spring, with the sock of fabric helping keep the main springs separated. Further still, whether using the baffle box 300 or individual socks, additional components may be present. For example, a slip cover (not specifically shown) may cover the baffle box 300 and/or individual socks, where the slip cover may provide a uniform exterior appearance. The slip cover may also couple to adjacent slip covers to tie together the rows to reduce the chances of objects slipping down between the rows and/or columns, and to enable a more uniform upper surface.

Each adjustable spring assembly 104 is designed and constructed such that the weight or force carried by each main spring 320 can be adjusted. Stated otherwise, each adjustable spring assembly 104 is designed and constructed such that the compression of each main spring 320 can be adjusted. That adjustment may take place when the main springs 320 are un-laden (e.g., when no persons or objects are on the sleeping surface 102), and the adjustment may take place when persons or objects reside on the sleeping surface 102. When the bed controller 118 (FIG. 1) determines a particular adjustable spring assembly 104 should carry more force, the motor 312 of the particular adjustable spring assembly 104 is activated to move the spring plate 318 away from the spring rail 302 and toward the sleeping surface 102 (FIG. 1). Moving the spring plate 318 away from the spring rail 302 and toward the sleeping surface 102 compresses the main spring 320 and thus the main spring 320 carries more weight or force. Oppositely, when the bed controller 118 determines a particular adjustable spring assembly 104 should carry less force, the motor 312 of the particular adjustable spring assembly 104 is activated to move the spring plate 318 toward the spring rail 302 and away from the sleeping surface 102. Moving the spring plate 318 toward the spring rail 302 and away from the sleeping surface 102 de-compresses the main spring 320 and thus the main spring 320 carries less weight or force.

While in some embodiments it is possible that the bed controller 118 may control force carried by each adjustable spring assembly 104 in an open-loop sense (e.g., without measuring the weight or force carried by each adjustable spring assembly), in yet still other cases the weight or force carried by each adjustable spring assembly 104 is measured by a force sensor. For example, a force sensing mat may be placed over the adjustable spring assemblies 104 after installation. In other cases, each adjustable spring assembly 104 may be associated with a dedicated force sensing mat (e.g., coupled to or forming the upper wall 326 of the baffle box 300). In yet still other cases, each adjustable spring assembly 104 may have an associated force sensor, such as by way of a strain gauge associated with the each motor 312.

Figure 4:
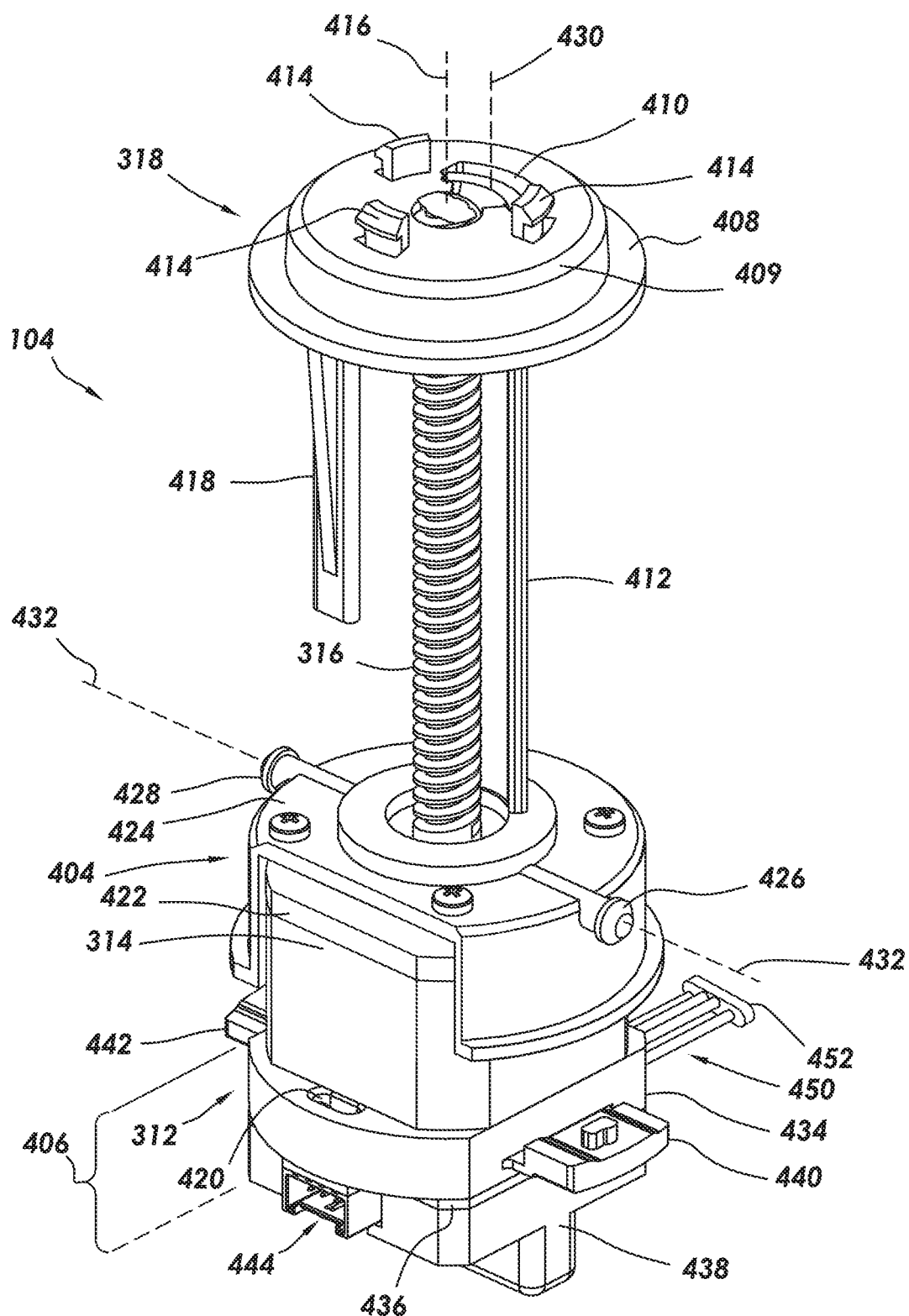
FIG. 4 shows a perspective view of an adjustable spring assembly (without the main spring), and in accordance with at least some embodiments.

FIG. 4 shows a perspective view of an adjustable spring assembly (without the main spring) in accordance with at least some embodiments. In particular, the example adjustable spring assembly 104 of FIG. 4 shows the motor 312, the lead screw 316, and the spring plate 318. The description turns first to the spring plate 318.

The spring plate 318 is coupled to the lead screw 316 as discussed above, with the precise type of coupling dependent upon how the lead screw 316 couples to the rotor of the motor 312 (e.g., captive and non-captive lead screw). The example spring plate 318 defines an annular shoulder 409 that circumscribes the location of the lead screw 316, and a stop, such as annular flange 408, that extends outward from below the annular shoulder 409. The lower end of the main spring 320 (not shown) couples to the spring plate 318 by telescoping over the annular shoulder 409 and resting on the annular flange 408. The example spring plate 318 further defines an anti-rotation aperture 410 through the spring plate 318 and disposed between the location of the coupling to the lead screw 316 and the annular shoulder 409. As the name implies, when present the anti-rotation aperture 410 works in conjunction with a post 412 to hold the spring plate 318 against rotation during periods of time when the motor 312 is turning the lead screw 316. The example spring plate 318 further comprises a set of spring clips 414 disposed on and radially spaced around an upper surface of the spring plate 318. FIG. 4 shows three spring clips, but one or more spring clips may be present. The spring clips 414 may be used to hold an additional and optional spring, referred to as a massage spring (discussed in greater detail below). The spring clips 414 are designed and constructed such that as the massage spring is pushed downward over the spring clips 414, the spring clips 414 may deflect slightly inward (e.g., deflect toward a longitudinal central axis 416 of the lead screw 316), and then snap over and hold the wire forming the lower-most loop of wire of the massage spring. Finally, the example spring plate 318 defines a zero-position post 418. The example zero-position post 418 extends downward from a lower surface of the spring plate 318. The example zero-position post 418 works in conjunction with a micro-switch (exposed through aperture 420, but not visible) to inform the motor controller when the spring plate 318 has reached is lowest or zero position (which may also be a position where the respective main spring carries the least force).

The motor 312 comprises the stator 314 as well as an upper or top plate 404 and a lower or bottom plate 406. The top plate 404 and bottom plate 406 hold the stator 314 together and in place. In the example embodiment of FIG. 4, the top plate 404 is a two-piece component comprising a metallic plate 422 directly abutting the stator 314, and an adapter 424 coupled over and abutting the metallic plate 422. The adapter 424 defines several additional features, such as the post 412 and the protrusions 426 and 428. In other cases, however, the top plate 404 may be an integral component defining all the various features (e.g., post 412 and protrusions 426 and 428). Hereafter, reference will be made to the top plate 404 with the understanding that any feature mentioned may be an integral portion of the top plate 404, or may be implemented by an adapter (e.g., adapter 424) coupled to the top plate 404. The post 412 extends upward from the top plate 404, and a longitudinal central axis 430 of the post 412 is parallel to the longitudinal central axis 416 of the lead screw 316. The post 412 works in conjunction with the anti-rotational aperture 410 to help hold the example spring plate 318 against rotation, and thus the post 412 may be referred to as an anti-rotation post 412.

Still referring to FIG. 4, the example top plate 404 further includes the buttons or protrusions 426 and 428. In example cases, the protrusions 426 and 428 share a longitudinal central axis 432, and the protrusions 426 and 428 extend outward in opposite directions from the top plate 404. The example longitudinal central axis 432 of the protrusions is perpendicular to the longitudinal central axis 416 of the lead screw 316. In some cases, the protrusions 426 and 428 are the locations to which the baffle box 300 (FIG. 3) couples at the location of each adjustable spring assembly 104.

In the example embodiment of FIG. 4, the bottom plate 406 is a multiple-component assembly comprising a mounting plate or suspension member 434, a control PCB 436, and cover piece 438. In example embodiments, the suspension member 434 is metallic and directly abuts the stator 314. The suspension member 434 is associated with a force sensor (not visible in FIG. 4), where the force sensor is configured to measure an amount of weight or force carried by the adjustable spring assembly 104. The example suspension member 434 defines two ears or tabs 440 and 442. The tabs 440 and 442 extend outward and in the same directions as the example protrusions 426 and 428. When the adjustable spring assembly 104 is coupled to a respective spring rail, the adjustable spring assembly 104 is suspended by the tabs 440 and 442, and more particularly the stator 314 and all the components above the stator are suspended above the tabs 440 and 442. Stated otherwise, when assembled the example adjustable spring assembly 104 is rigidly coupled to the spring rail by way of the tabs 440 and 442, and the adjustable spring assembly 104 is suspended above the bottom plate 406. Other coupling mechanisms are also possible.

The example bottom plate 406 further comprises the control PCB 436 sandwiched between the suspension member 434 and the cover piece 438. In example embodiments, electrical connections between various components may be made merely by coupling the three components together. For example, a motor controller disposed on the control PCB 436 may be electrically coupled to electrical pins within a connector (e.g., connector 444) and the windings of the stator 314 of the motor 312 by stacking the three components together. In other cases, the cover piece 438 may be omitted, and the control PCB 436 may be fully or partially exposed on the bottom side of the adjustable spring assembly 104. The electrical aspects of control of the adjustable spring assembly are discussed in greater detail below. Each adjustable spring assembly 104 comprises a pig tail or electrical cable 450 and corresponding electrical connector 452. Thus, the electrical connector 452 is designed and constructed to couple to a corresponding electrical connector 444 of an immediately adjacent adjustable spring assembly 104.

Figure 5:
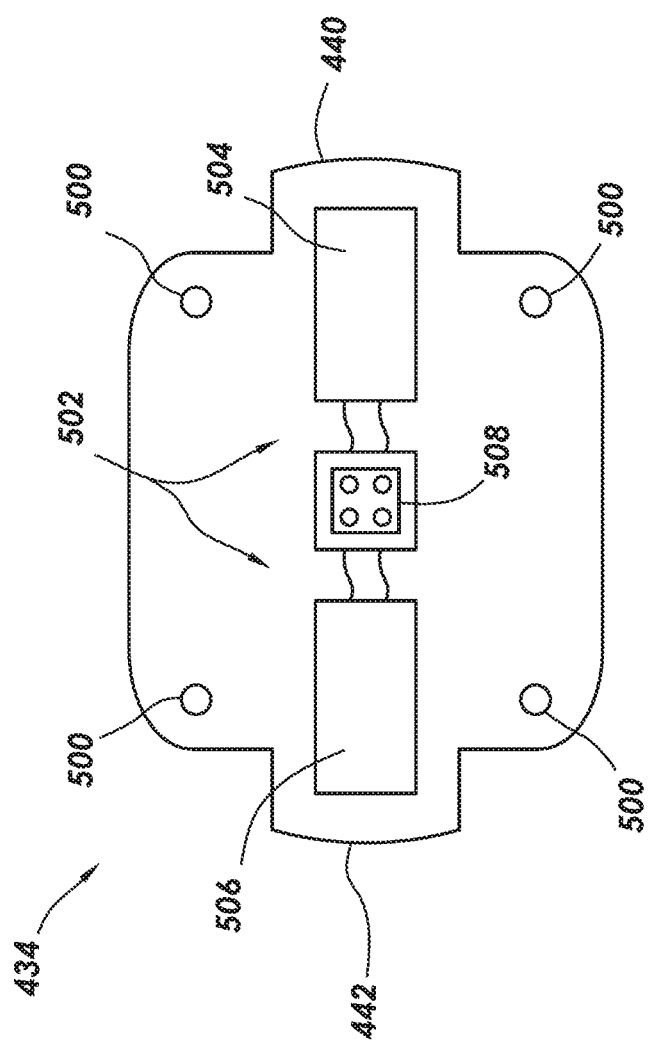
FIG. 5 shows a bottom view of the suspension member in accordance with at least some embodiments.

FIG. 5 shows a bottom view of the suspension member 434 in accordance with at least some embodiments. In particular, the example suspension member 434 includes the tabs 440 and 442 extending outward, along with through bores 500. Affixation devices (e.g., screws) that are not shown extend through the through bores 500 to couple the suspension member 434 to the stator 314 (FIG. 3). Within the main body of the suspension member 434 there is a force sensor 502 in the example form a first strain gauge 504 associated with the tab 440 and second strain gauge 506 associated with tab 442. Together the strain gauges 504 and 506 are designed and constructed to measure the weight or force carried by suspension member 434, and thus carried by the adjustable spring assembly 104. More particularly, strain gauge 504 measures strain associated with tab 440, and strain gauge 506 measures strain associated with tab 442. The total weight or force carried may thus be calculated based on the strain associated with tabs 440 and 442. Having two strain gauges is merely an example, and any suitable force sensor that measures weight or force carried may be used. The force sensor 502 is operationally coupled to the bed controller 118 (FIG. 1) by way of the control PCB 436 (FIG. 4). In example embodiments the force sensor 502 electrically couples to the control PCB 436 by way of electrical connector 508. That is, the electrical connector 508 is designed and constructed such that aligning the control PCB 436 with the suspension member 434, and then abutting the control PCB 436 against the suspension member 434, mechanically and electrically couples the electrical connector 508 to a mating connector on the control PCB 436 (the mating connector not shown in FIG. 5). The force sensor 502 (and control PCB 436) provide a value indicative of force to the bed controller 118. Thus, when an adjustable spring assembly 104 is mechanically coupled to a spring rail, the force carried by the adjustable spring assembly 104 is measured by the force sensor 502 (and other circuits on the control PCB 436).

Returning to FIG. 3, the motor 312 is affixed to the spring rail 302 by being mechanically coupled to the spring rail 302. In at least some example embodiments, affixing the motor 312 to the spring rail 302 comprises rotating the motor 312 relative to the spring rail, the rotation about the longitudinal central axis of the lead screw 316, to engage elements (e.g., the tabs 440 and 442 shown in FIG. 4) of the suspension member 434 to the spring rail 302.

Figure 6:
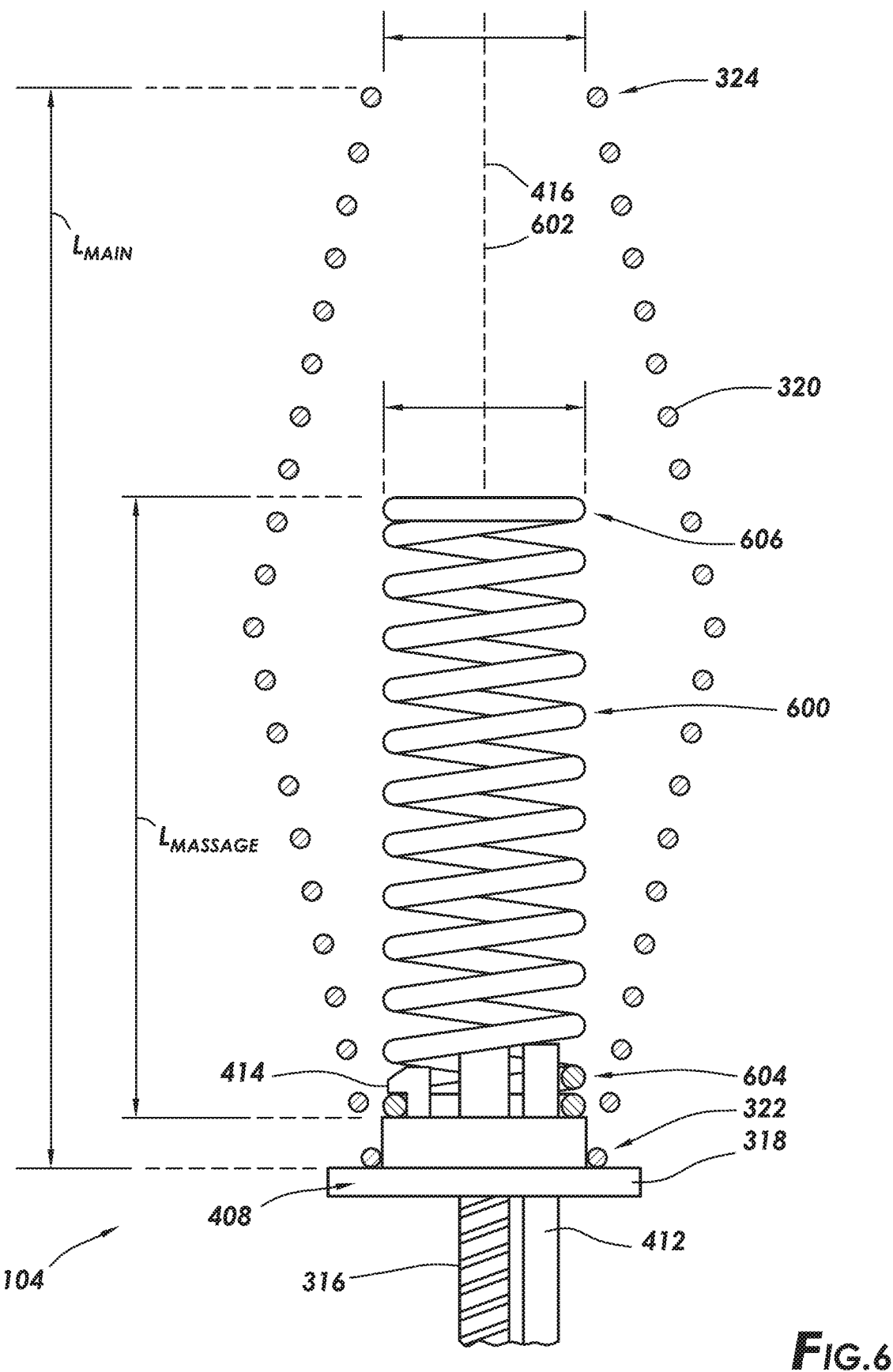
FIG. 6 shows a side elevation, partial cross-sectional view, of a portion of an adjustable spring assembly in accordance with at least some embodiments.

FIG. 6 shows a side elevation, partial cross-sectional view, of a portion of an adjustable spring assembly in accordance with at least some embodiments. In particular, shown in FIG. 6 is a side elevation view of the spring plate 318 coupled to the lead screw 316 and in operational relationship to the post 412. The components of the adjustable spring assembly below the lead screw 316 and post 412 are omitted to provide further detail regarding the springs. In at least some embodiments each adjustable spring assembly 104 comprises two springs—the main spring 320 and a massage spring 600 placed concentrically within the main spring 320. In FIG. 6, the main spring 320 is shown in cross-section to reveal the internal massage spring 600. The main spring 320 is a coil or helical spring that couples on the first end 322 by telescoping over the spring plate 318 and resting on the annular flange 408. The lead screw 316 defines the longitudinal central axis 416, and the main spring 320 (in spite of being barrel shaped) has a central axis that is coaxial with the longitudinal central axis 416. The optional massage spring 600 defines a central axis 602 that is coaxial with the central axis of the main spring 320, and thus coaxial with the longitudinal central axis 416 of the lead screw 316. In other cases, however, the massage spring 600 may be shifted such that the central axis of the massage spring 600 is parallel to, but not coaxial with, the remaining central axes.

The massage spring 600 defines a lower end 604 and an upper end 606. The lower end 604 in the example systems is coupled to the spring plate 318 by way of the spring clips 414. Only one spring clip 414 is shown in FIG. 6, but more than one may be used. It is noted that the lower end 604 of the massage spring 600 is also shown in partial cross-section to reveal the spring clip 414 clipping over and holding the lower end 604 against the upper surface of the spring plate 318. As illustrated by FIG. 6, the main spring 320 defines an uncompressed or un-laden length $L_{MAIN}$, with the length as discussed above. The massage spring 600 likewise defines an uncompressed or un-laden length $L_{MASSAGE}$ that is less than the $L_{MAIN}$. When the length $L_{MAIN}$ is about 10 inches, the length $L_{MASSAGE}$ may be between and including 4 inches and 8 inches, and in some cases between and including 5 inches and 6 inches. In some cases, the massage spring 600 has spring constant greater than the spring constant of the main spring 320, but in other cases the spring constant of the massage spring 600 may be the same or smaller than the spring constant of the main spring 320. In accordance with example systems, the massage spring 600 is used in conjunction with movement of the spring plate 318 to implement an additional massage function for the overall adjustable sleeping system 100 (FIG. 1). In particular, under command of the bed controller 118 (FIG. 1), the adjustable spring assembly 104 may quickly drive the spring plate 318 upward to fully compress the main spring 320, and thus enabling the upper end 606 of the massage spring 600 to extend at least to the second end 324 of the main spring 320, and in some cases extend above the second end 324 of the main spring 320, to provide a more concentrated force to the body of person of the adjustable sleeping system 100. It follows that the spring constant of the massage spring 600 is higher than the spring constant of the main spring 320. It is to be understood that implementing a massage function is not predicated on the presence of the massage spring 600. Rather, a massage function (discussed more below) may be implemented in the absence of the massage spring by selectively driving the main spring 320 to carry more, and then less, force.

Commercially available beds differ in many respects, but the primary differentiator is firmness. The measure of firmness differs by manufacturer, but in most cases firmness is judged along a spectrum from very soft (sometimes "extra plush") to extra firm. The example adjustable sleeping system 100 may emulate the entire firmness spectrum. In particular, for a very soft setting the bed controller 118 may command all the adjustable spring assemblies 104 to retract their respective spring plates 318 to the position closest to the respective motors 312 (e.g., the zero position discussed above). Thus, the user of the bed takes advantage of the lower spring constant of the main spring 320. Oppositely, for a very firm setting the bed controller 118 may command the adjustable spring assemblies 104 to move their respective spring plates 318 to the position closest to the second ends 324 of the main spring 320. As discussed above, the pockets of the baffle box 300 and/or the slip cover limit spring travel, and thus the springs are partially compressed against the baffle box 300. Thus, for a firm or extra firm setting the user of the bed takes advantage of the main spring 320 being fully compressed and/or the extra support of the massage spring 600.

While possible that the adjustable spring assemblies 104 could be used solely to implement firmness across the entire bed, the individually addressable and controllable adjustable spring assemblies 104 provide better granularity of control. In particular, in addition to or in place of the firmness adjustability, example embodiments implement any of a number of force control and/or force normalization routines. Such control is implemented and/or supervised by the bed controller 118 communicating with each individual adjustable spring assembly 104. The specification turns to example communicative structures.

Figure 7:
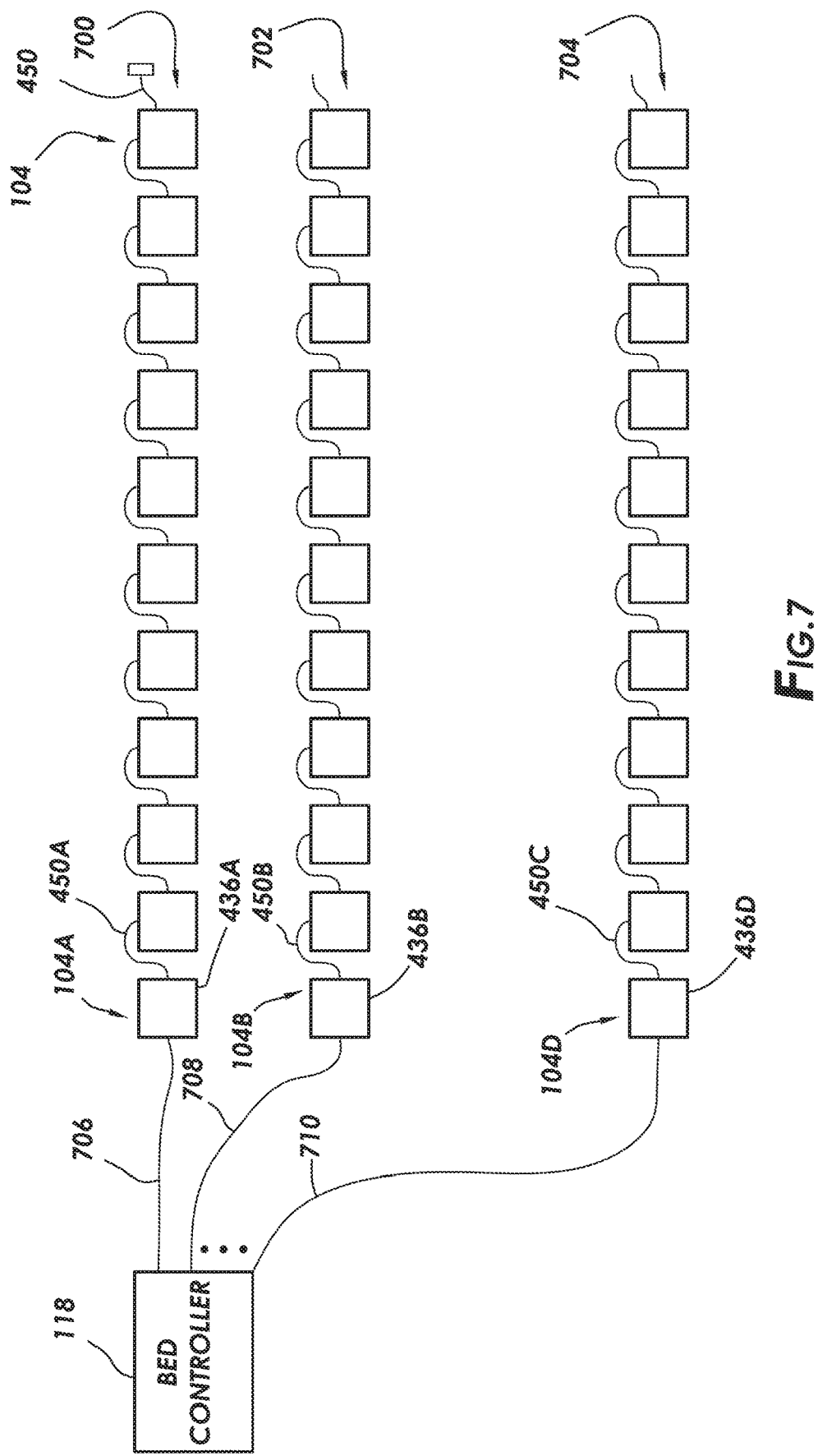
FIG. 7 shows an electrical block diagram of the adjustable sleeping system in accordance with at least some embodiments.

FIG. 7 shows an electrical block diagram of the adjustable sleeping system in accordance with at least some embodiments. In particular, FIG. 7 shows the bed controller 118 and three example rows of adjustable spring assemblies 104. The reference number scheme of FIG. 7 regarding the adjustable spring assemblies 104 corresponds to FIGS. 1 and 2 to help correlate location within the array of adjustable spring assemblies 104. Only three rows of adjustable spring assemblies 104 are shown so as not to unduly complicate the figure, the rows labeled 700, 702, and 704. Within each row resides a series or set of adjustable spring assemblies 104, and the blocks within each row more particularly represent the respective control PCBs 436 of each adjustable spring assembly 104. Thus, example control PCB 436A is a member of the adjustable spring assembly 104A. Example control PCB 436B is a member of the adjustable spring assembly 104B. Example control PCB 436C is a member of the adjustable spring assembly 104C.

The bed controller 118 is communicatively coupled to each row 700, 702, and 704 by a respective communications cable 706, 708, and 710. The communications cable may take any suitable form depending the communications protocol implemented. The communications cables 706, 708, and 710 may contain electrical conductors, optical conductors, and/or combinations of the electrical and optical conductors. The protocol used to communicate from the bed controller 118 to the control PCBs likewise may take any suitable form. In one example system, the communications protocol used between the bed controller 118 and the control PCBs is the Institute of Electrical and Electronics Engineers (IEEE) RS485 serial communication protocol. However, other communications protocols, including packet-based messaging protocols. In other cases, the communication cables 706, 708, and 710 can be omitted and the system may use a wireless communications protocol (e.g., IEEE 802.11, Bluetooth).

The example adjustable spring assemblies along a row are communicatively coupled together in a daisy-chain fashion, as shown in FIG. 7. For example, the first adjustable spring assembly 104A in row 702 is communicatively coupled to an immediately adjacent or nearest neighbor (along the row) adjustable spring assembly by way of the electrical cable 450A. The adjacent adjustable spring assembly is coupled to its nearest neighbor (along the row) adjustable spring assembly 104 way of its electrical cable 450, and so on, along the row 702. Because the adjustable spring assemblies 104 are modular components, and thus may be placed in any row and at any location along the row, the final adjustable spring assembly 104 in row 702 likewise has its electrical cable 450, but that final electrical cable 450 remains unconnected (or may include a termination connector to reduce signal reflections). Thus, the bed controller 118 may communicate with any adjustable spring assembly 104 in row 700 by communicating directly with adjustable spring assembly 104A, and communication indirectly (through intervening adjustable spring assembly or assemblies 104) with other adjustable spring assembly in the row 700. It follows that the bed controller 118 may communicate with any adjustable spring assembly in any row in a similar fashion.

The organization of the array of adjustable spring assemblies 104 in rows for assembly and communication purposes is merely an example. The assembly and communication scheme could be organized along columns rather than rows. In other cases, the assembly and communication scheme may take any suitable form, such as a saw-tooth pattern if the adjustable spring assemblies are arranged in a honeycomb pattern. Further still, the communications organization may be conceptually disconnected from the assembly organization. For example, in the honeycomb pattern the nearest neighbor adjustable spring assemblies may reside along slanted rows (slanted relative to the length and width) regardless of how the adjustable spring assemblies are physically assembled together. The specification now turns to a more detailed description of an example bed controller 118.

Figure 8:
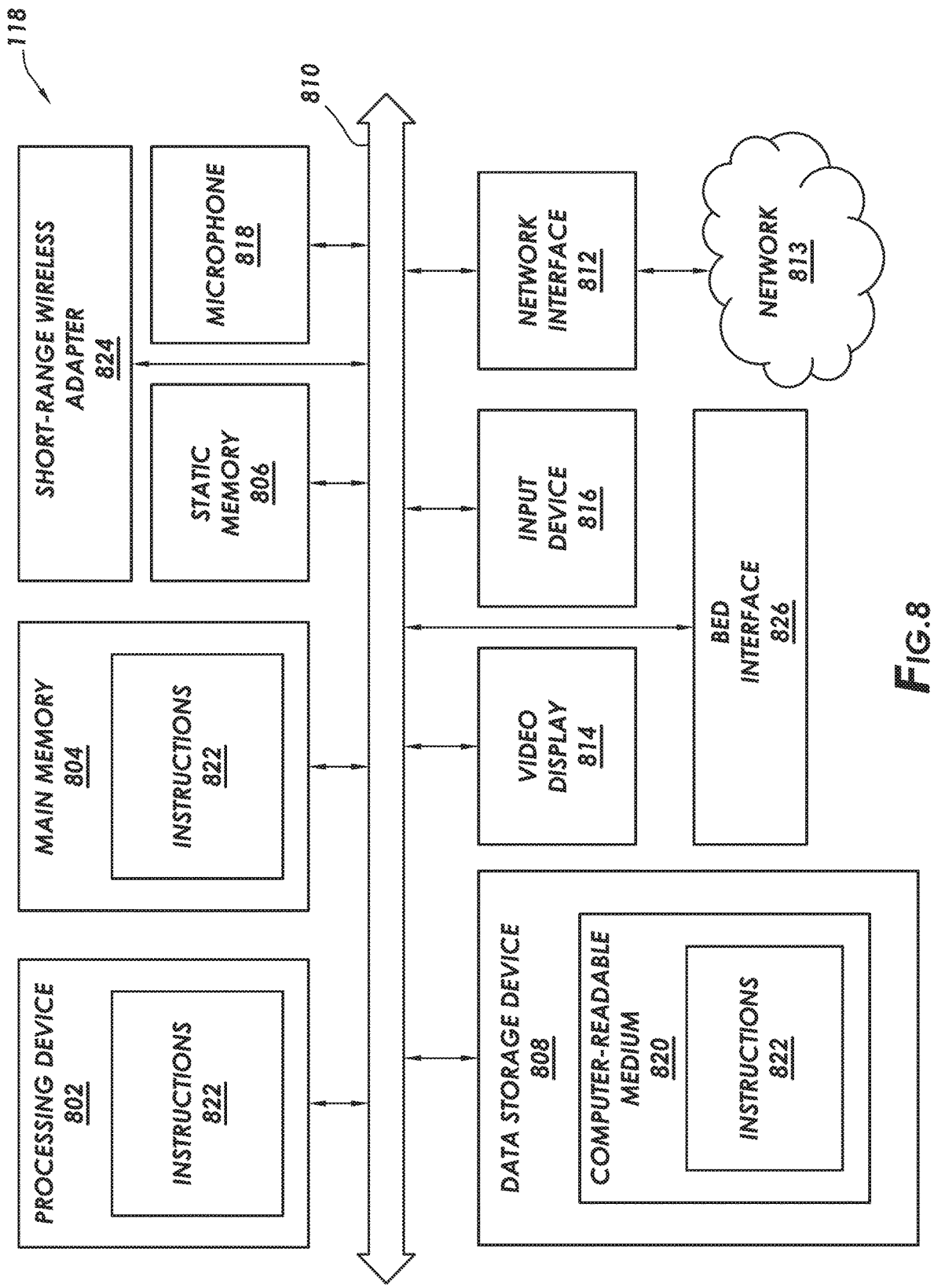
FIG. 8 shows an electrical block diagram of a bed controller in accordance with at least some embodiments.

FIG. 8 shows an electrical block diagram of a bed controller in accordance with at least some embodiments. In particular, one example bed controller 118 is implemented as a computer system. The computer system may be connected (e.g., networked) to other computer systems in a local area network (LAN), an intranet, an extranet, or the Internet. Further, while only a single computer system is illustrated, the term "computer" shall also be taken to include any collection of computers (e.g., two bed controllers, one each for two twin size beds placed side-by-side) that individually or jointly execute a set (or multiple sets) of instructions to perform control of the adjustable spring assemblies 104.

The example bed controller 118 comprises a processing device 802, a main memory 804, and a static memory 806, all communicatively coupled by way of bus 810. The main memory 804 may be read-only memory (ROM), flash memory, and/or dynamic random access memory (DRAM) such as synchronous DRAM (SDRAM). The static memory 806 may be flash memory, ROM, and/or static random access memory (SRAM).

Processing device 802 represents one or more general-purpose processing devices such as a microprocessor, central processing unit, or the like. More particularly, the processing device 802 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 802 may also be one or more special-purpose processing devices such as an application specific integrated circuit (ASIC), a field programmable gate array (FPGA), a digital signal processor (DSP), network processor, or the like. The processing device 802 is configured to execute instructions for performing any of the force control aspects and/or massage function aspects of the adjustable spring assemblies 104, with specific examples discussed in great detail below.

The example bed controller 118 may further include a network interface device 812. The bed controller 118 also may include a video display 814 (e.g., a liquid crystal display (LCD) or a cathode ray tube (CRT)), one or more input devices 816 (e.g., a keyboard and/or a mouse), and one or more microphones 818 (e.g., to listen for snoring, or to receive voice commands). In one illustrative example, the video display 814 and the input device(s) 816 may be combined into a single component or device (e.g., an LCD touch screen).

The data storage device 808 may include a computer-readable medium 820 on which the instructions 822 embodying any one or more of the functions described herein are stored. The instructions 822 may also reside completely, or at least partially, within the main memory 804 and/or within the processing device 802 during execution thereof by the processing device 802 of the bed controller 118. As such, the main memory 804 and the processing device 802 also constitute computer-readable media. The instructions 822 may further be transmitted or received over a network 813 via the network interface device 812.

The example bed controller 118 further comprises a short-range wireless adapter 824 to enable communication with the portable computing system (e.g., smart phone or tablet device) of a person residing on the adjustable sleeping system 100 (FIG. 1). The short-range wireless adapter 824 may implement any suitable wireless communication protocol, or multiple communications protocols. For example, the short-range wireless adapter 824 may implement Bluetooth, or one of the many variants of the IEEE 820.11 protocol. Using these or other protocols, the bed controller 118 may receive commands from a person residing on the adjustable sleeping system 100, for example to receive an indication to implement a force control function (e.g., increase or decrease firmness, begin or end a massage function, select a particular body portion (less than the entire body) to receive special treatment).

Finally, the example bed controller 118 further comprises one more bed interfaces 826 coupled to the bus 810. That is, in cases where the communication protocol used to couple to the network 813 is different than a communication protocol used to communicate with the adjustable spring assemblies 104, additional bed interfaces 826 may be used. In the example system, the communication protocol used to communicate with the adjustable spring assemblies is the IEEE RS485 serial communication protocol, and thus the bed interface 826 may implement the RS485 protocol.

Figure 9:
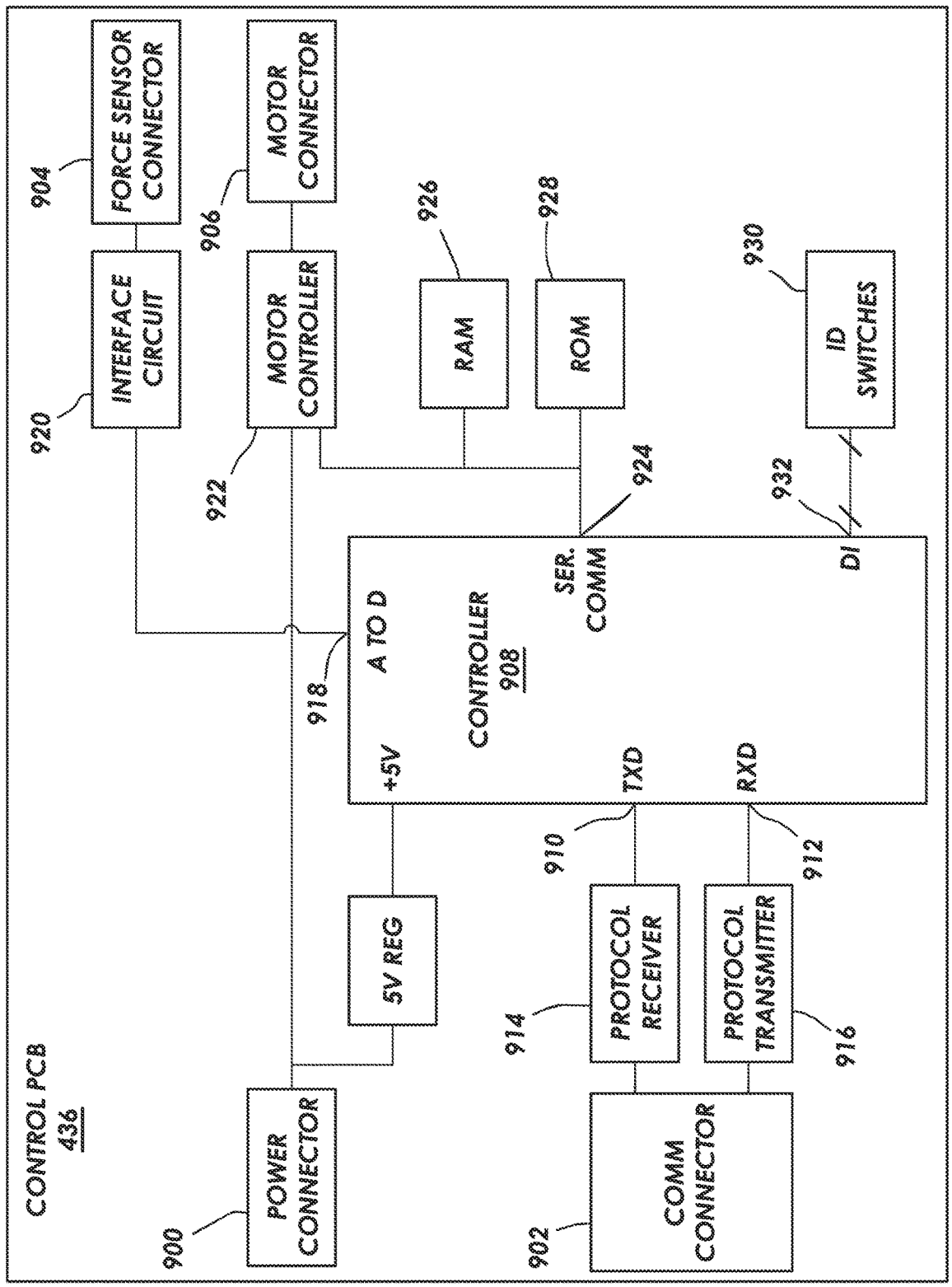
FIG. 9 shows an electrical block diagram of the control PCB in accordance with at least some embodiments.

FIG. 9 shows an electrical block diagram of the control PCB in accordance with at least some embodiments. In particular, the example control PCB 436 interfaces with components off the control PCB 436 by way of a plurality of connectors, such as power connector 900, communication connector 902, force sensor connector 904, and motor connector 906. The power connector 900 may couple to both upstream and downstream adjustable spring assemblies, and thus may be electrically connected to both the externally accessible electrical connector 444 (FIG. 4) and electrical cable 450 (FIG. 4). In example cases, the control PCB 436 is provided DC power (e.g., 12 VDC) to power the various components on the control PCB 436. Similar to the power connector 900, the communication connector 902 may couple to both upstream and downstream adjustable spring assemblies, and thus may be electrically connected to both the externally accessible electrical connector 444 and electrical cable 450. The load cell connector 904 is designed and constructed to couple the mating electrical connector 508 (FIG. 5) associated with the force sensor 502 (also FIG. 5). And finally, the motor connector 906 is designed and constructed to couple to the winding or windings disposed within the stator 314 of the motor 312 (both FIG. 3).

In example systems, each control PCB 436 includes a controller 908 (e.g., a PIC16F19155 microcontroller available from Microchip Technology Inc. of Chandler, Ariz.). The example controller 908 defines a plurality of input and output ports. For example, the controller 908 defines a transmit port 910 and a receive port 912. In the example system, the transmit port 910 couples to a protocol receiver 914, and the receive port 912 couples to a protocol transmitter 916. In example systems, the protocol receiver 914 and the protocol transmitter 916 implement a communication protocol, such as the IEEE RS485 serial communication protocol discussed above. By way of the communication protocol, the bed controller 118 (FIGS. 1 and 8) may command the controller 908 to take action, such as increasing or decreasing the weight or force carried by the adjustable spring assembly 104 within which the controller 908 is implemented.

The controller 908 further includes an analog-to-digital (A/D) input port 918. In the example system, the A/D input port 918 may be used to read values indicative of force from the force sensor 502. In particular, the example system comprises an interface circuit 920 electrically disposed between the A/D input port 918 and the connector 904 (and thus the force sensor 502). The interface circuit 920 may implement circuits used to power and/or read the force sensor 502. The precise nature of the interface circuit 920 depends on the type of force sensor 502 implemented. In an example case the interface circuit 920 implements a differential amplifier, with the type of differential amplifier dependent upon the precise nature of the force sensor 502. While in the example system the interface circuit 920 couples to the controller 908 by way the A/D input port 918, other communication systems may be used (e.g., serial interface).

Still referring to FIG. 9, the example control PCB 436 further comprises a motor controller 922. The motor controller 922 is electrically coupled to, and receives power from, the power connector 900. The motor controller 922 couples to the motor connector 906, and thus when assembled into an adjustable spring assembly 104 the motor controller 922 couples to the winding or windings of the motor 312. The precise nature of the motor controller 922 depends on the type of motor 312 implemented within the adjustable spring assembly 104.

The controller 908 defines a serial communication port 924, and in the example system the controller 908 communicates with the motor controller 922 over the serial communication port 924. The serial communication port 924, and related protocol, may take any suitable form (e.g., a serial peripheral interface (SPI)). In other cases, the controller 908 may be communicatively coupled to the motor controller 922 by any suitable communication systems, including by sending and/or receiving analog signals to/from the motor controller 922.

The controller 908 in some cases has onboard random access memory (RAM) and non-volatile storage (e.g., read-only member (ROM)), but in the example system the controller PCB 436 also implements external RAM 926 and external ROM 928. The example RAM 926 and ROM 928 are communicatively coupled to the controller 908 by way of the serial communication port 924, but any suitable communication system and protocol may be used. The RAM 926 may be used to store programs executed by a processor of the controller 908 (the processor not specifically shown), and in some cases the RAM 926 may be the working memory for the controller 908. Further still, the RAM 926 itself may implement a non-volatile aspect (e.g., the RAM 926 may be static RAM (SRAM)). The ROM 928 may likewise be used to store programs executed by a processor of the controller 908, including the underlying operating system and basic input-output system (BIOS) services. The ROM 928 may take any suitable form, such as an electrically-erasable programmable ROM (EEPROM).

Still referring to FIG. 9, the example control PCB 436 further comprises a set of identification switches 930 coupled to the controller 908. In the example system the controller 908 defines a plurality of digital inputs 932. By way of the digital inputs 932, the controller 908 may read the on/off state of each switch of the identification switches 930. Using the identification switches 930, the controller 908, and thus the control PCB 436 and overall adjustable spring assembly, can be uniquely identified by the bed controller 118. In other cases, however, identification of each adjustable spring assembly make take place programmatically (e.g., reading a unique media access control (MAC) address from each control PCB), and thus the identification switches 930 may be omitted, or used for other functions. For example, the switches may be used to identify membership in a particular row, or the switches may be used to identify the first adjustable spring assembly in a row (e.g., of FIG. 7, row 700 or row 702) when the communication protocol relies on communicatively daisy-chaining of the adjustable spring assemblies 104.

The specification now turns more specifically to example methods of operation of the adjustable sleeping system 100. The bed controller 118 may be designed, constructed, and/or programmed to implement a host of beneficial methods or functions using the adjustable nature of the adjustable spring assemblies 104. In some embodiments the functionality described below is software or instructions stored on a memory (e.g., data storage device 808) and executed by processing device 802 of the bed controller 118. In other cases, the bed controller 118 may program the controllers 908 of the control PCBs 436 to perform some or all the functionality. In other cases, the functionality may be "hardwired" into the bed controller 118, such as by burning a field programmable gate array (FPGA), alone or combination with other systems. In yet still other cases, the functionality may be software on the user's mobile computing device (e.g., mobile phone, tablet device) that sends commands to the bed controller 118 and the controllers 908 (through the bed controller 118).

At the highest conceptual level, the bed controller 118 may implement control and/or adjustment of firmness across the entire sleeping surface 102 of the adjustable sleeping system 100. For example, the bed controller 118 may receive a command to adjust the entire sleeping surface 102 to a particular firmness setting, the firmness setting selected from a range of settings along a spectrum from extra plush to extra firm. Based on the selected overall firmness, each adjustable spring assembly 104 may be driven to implement the desired firmness. More particularly, the bed controller 118 may command each adjustable spring assembly 104 to drive their respective spring plates 318 to the same or about the same positions relative to any consistent reference (e.g., relative to the sleeping surface 102 if no person or object resides on the bed, or relative to the top plate 404 of each motor 312). The driving of the spring plates 318 to implement the selected overall firmness setting may also take place when the person resides on the sleeping surface 102.

In addition to, or in place of, adjusting firmness across the entire adjustable sleeping system 100, example embodiments may implement force control by the adjustable spring assemblies 104 beneath a person residing on the sleeping surface 102. The specification thus turns to a description of sensing an area of the sleeping surface upon which a person resides, and then turns to example force control features.

Figure 10:
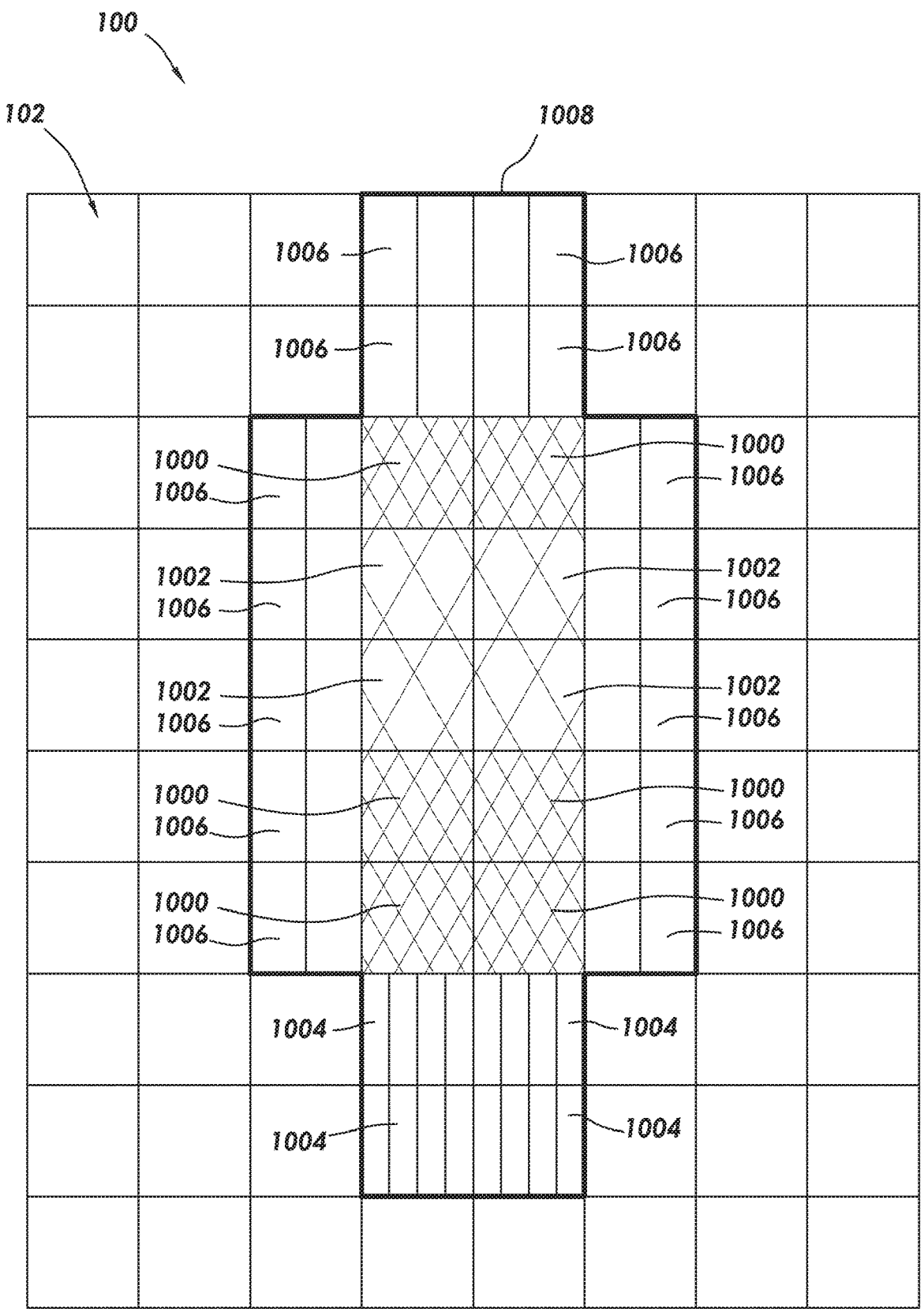
FIG. 10 shows an overhead view of the sleeping surface of an adjustable sleeping system, in accordance with at least some embodiments.

FIG. 10 shows an overhead view of the sleeping surface 102 of an adjustable sleeping system 100, in accordance with at least some embodiments. In particular, the example sleeping surface 102 is conceptually, though not necessarily physically, divided into a grid with each square in the grid representing the location of an adjustable spring assembly 104. The size of the squares representing the locations of the adjustable spring assemblies 104 is exaggerated for clarity. Consider that initially nobody is laying on the sleeping surface 102. The bed controller 118 (FIG. 1) may have each adjustable spring assembly 104 set to implement a particular firmness setting (either selected or a default setting). Once a person lays down on the sleeping surface 102, at locations where the person resides the respective adjustable spring assemblies 104 carry more force. As the human body has a shape, a contour, and a weight distribution, the force carried varies over the sleeping surface 102. For example, more force will be carried by the adjustable spring assemblies 104 beneath the torso of the person, and likewise more force will initially be carried by the adjustable spring assemblies 104 beneath the buttocks of the person.

FIG. 10 shows an example loading, with grid squares with more dense shading representing areas of higher force carried. For example, grids 1000 represent areas of highest force carried, grids 1002 represent next highest force carried, grids 1004 represent next highest force, and grids 1006 represent the lowest force carried. The four contiguous grids 1000 may be the location of the buttocks, the two contiguous grids 1000 may be the upper torso, and grids 1004 may be the legs. The upper four grids 1006 may be the head, and the grids 1006 along each side of the body may be the arms or are only partially beneath the person. The remaining grids carry no weight (beyond the weight of sheets, blankets, pets, and the like).

In accordance with at least some embodiments, the adjustable sleeping system 100 senses an area of the sleeping surface 102 upon which a person resides, the area being less than the entire area of the sleeping surface 102. For example, area 1008 is shown in dark lines as an example area within the sleeping surface 102. In example cases where each adjustable spring assembly 104 implements a force sensor 502 (FIG. 5), the sensing may be by the bed controller 118 reading a force value from each adjustable spring assembly 104 in the array. In cases in which no force gauges are implemented, sensing the sleeping area may involve commanding each adjustable spring assembly 104 to make a movement of predetermined distance of their respective spring plates 318 (e.g., driving the spring plates 318 toward the sleeping surface 102 a predetermined distance), and measuring an amount of electrical current drawn by each motor 312 to accomplish the task. Higher current used to move a spring plate 318 may be indicative of higher force carried by the adjustable spring assembly 104. Regardless of how the force is determined, the adjustable sleeping system 100 senses the area 1008 of the sleeping surface 102 upon which the person resides. Using the information about the area, the adjustable sleeping system 100 may drive a plurality of adjustable spring assemblies 104, the plurality being the adjustable spring assemblies beneath the area 1008, to control force distribution among the plurality of adjustable spring assemblies 104. The control of force distribution may implement any one of a number of methods and functions. The description starts with a force normalization and/or force averaging.

One example control of force distribution is force averaging. Implementing force averaging redistributes the force such that the weight or force carried by each adjustable spring assembly 104 of the plurality of adjustable spring assemblies 104 supporting the person is uniform. For example, the adjustable spring assemblies 104 associated with grids 1000 carrying the highest force will adjust by moving their spring plates 318 (FIG. 3) toward their motors 312 (FIG. 3), thus providing less force. Adjustable spring assemblies 104 carrying less weight or force (e.g., spring assemblies associated with grids 1004 and 1006) will adjust by moving their spring plates 318 toward the sleeping surface 102, thus providing or carrying more force. Stated differently, adjustable spring assemblies 104 initially in high force areas will adjust toward the plush end of the spectrum, while adjustable spring assemblies 104 in the low force areas will adjust toward to the firm end of the spectrum, all in an effort to normalize the force carried. Force averaging reduces "hot spots" that cause discomfort, and thus sleeping position changes. Reduction of "hot spots" also reduces bed sores common for bed-bound patients.

In accordance with example embodiments, implementing the force averaging may involve calculating (e.g., by the bed controller 118) an average force value carried by the plurality of adjustable spring assemblies 104 beneath the area 1008, the calculation prior to making any correction. With the average force value calculated, the example method then comprises driving (e.g., by command of the bed controller 118) each of the plurality of adjustable spring assemblies 104 to carry a force about equal to the average force value. More specifically still, in accordance with example embodiments the force averaging method may comprise determining that a person has laid on the sleeping surface 102. The example method then reads the force carried by each adjustable spring assembly 104, and excludes the adjustable spring assemblies 104 not involved in carrying the weight or force of the person (i.e., determines the area 1008). With the force values from the remaining adjustable spring assemblies 104 carrying force, the example method calculates an average force value, being the sum of the force values from the plurality of adjustable spring assemblies 104 beneath the area 1008 divided by the number of the plurality of adjustable spring assemblies 104 (and hereafter just "average force"). The example method then instructs each of the plurality of adjustable spring assembly 104 to adjust to carry a force equal or about equal to the average force. Having each adjustable spring assembly 104 carry a force exactly equal to the average force may not be practical, may cause oscillations, and because of slight variations in motor 312 performance and spring constants may not be possible. Thus, in some cases the example method instructs each adjustable spring assembly of the plurality of adjustable spring assemblies 104 to adjust to carry a force within a range or window of values around the average force. The intelligence for making the determination regarding the range or window of values may reside in the bed controller 118 (FIG. 1). In other cases, the bed controller 118 may instruct or program the control PCB 436 of each adjustable spring assembly 104 with the range of values, and set each control PCB 436 to the task of adjusting. Moreover, the example method may make the adjustments in phases, first adjusting with large granularity, recalculating the average value, and then adjusting with finer granularity, and so on.

The force averaging aspects are agnostic to position of the person (e.g., face up, face down, left side, or right side) on the sleeping surface 102. However, in example embodiments the granularity of the force values provides sufficient information to determine more than just the area upon which the person resides. In particular, in further example embodiments the bed controller 118 is able to determine body position, and certain additional functions may be implemented with the body position information. The specification now turns to determination of position of the person, and features that may be implemented when position is known.

Figure 11:
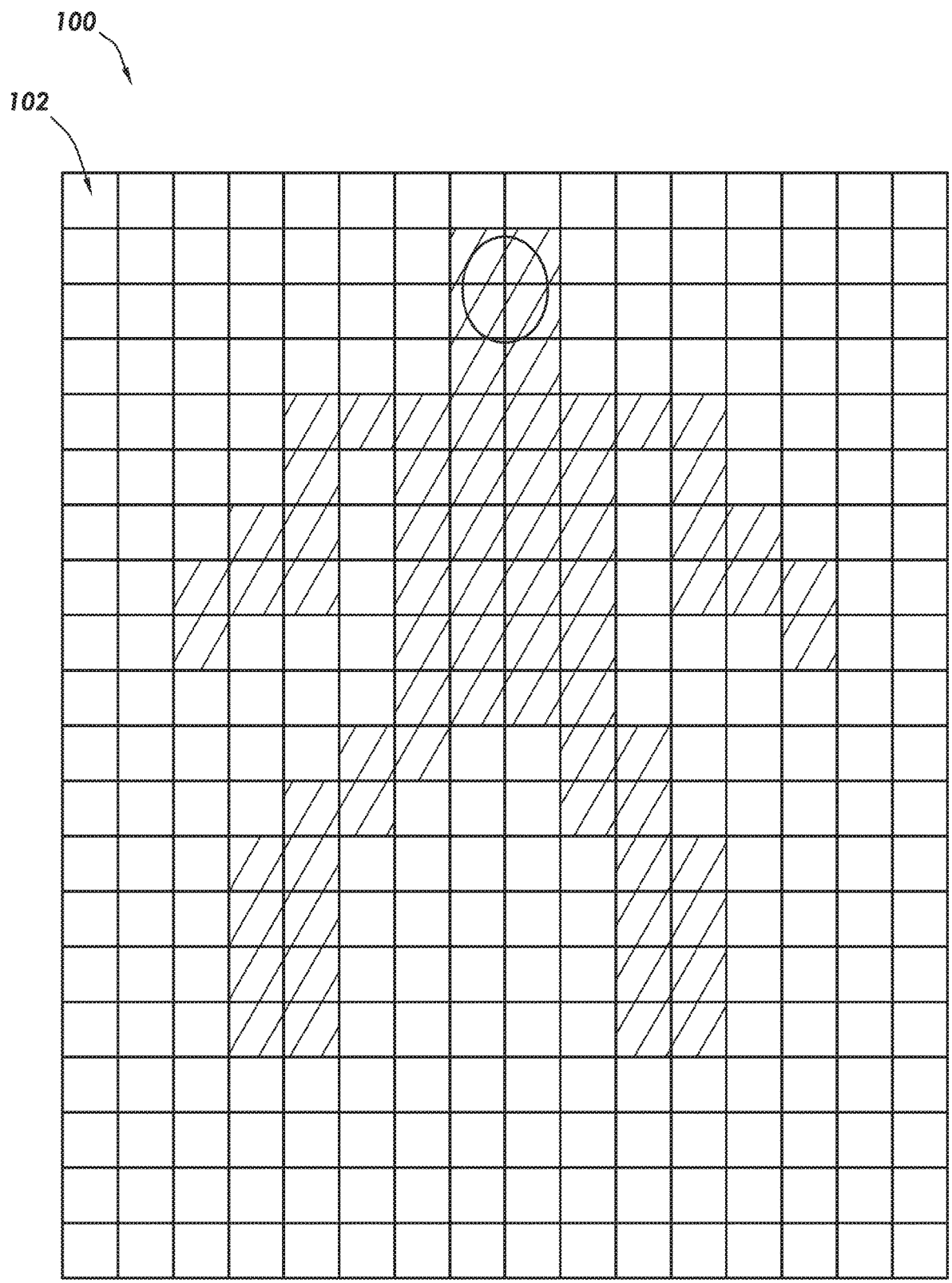
FIG. 11 shows an overhead view of the sleeping surface of an adjustable sleeping system, in accordance with at least some embodiments.

FIG. 11 shows an overhead view of the sleeping surface 102 of an adjustable sleeping system 100, in accordance with at least some embodiments. Again, the sleeping surface 102 is conceptually, though not necessarily physically, divided into a grid with each square in the grid representing the location of an adjustable spring assembly 104. The size of the squares representing the locations of the adjustable spring assemblies 104, though denser than FIG. 10, is nevertheless exaggerated for purposes of clarity. In particular, consider that initially nobody is laying on the sleeping surface 102. The bed controller 118 may have each adjustable spring assembly 104 set to implement a particular firmness setting (either selected or a default setting). Once a person lays on the bed, at locations where the person resides the plurality of adjustable spring assemblies 104 beneath the person carry more force. FIG. 11 shows an example loading with a person laying in a face-up sleeping position, with adjustable spring assemblies carrying load shown in shading. The shading is uniform in FIG. 11 so as not to unduly complicate the figure, but the force distribution would again track the contours and weight distribution of the user (prior to force normalization, if implemented). In some cases, distinguishing sleeping position may take into account force distribution (e.g., to distinguish face up from face down). Visible in the example force distribution of FIG. 11 are the user's head, arms, torso, and legs.

Figure 12:
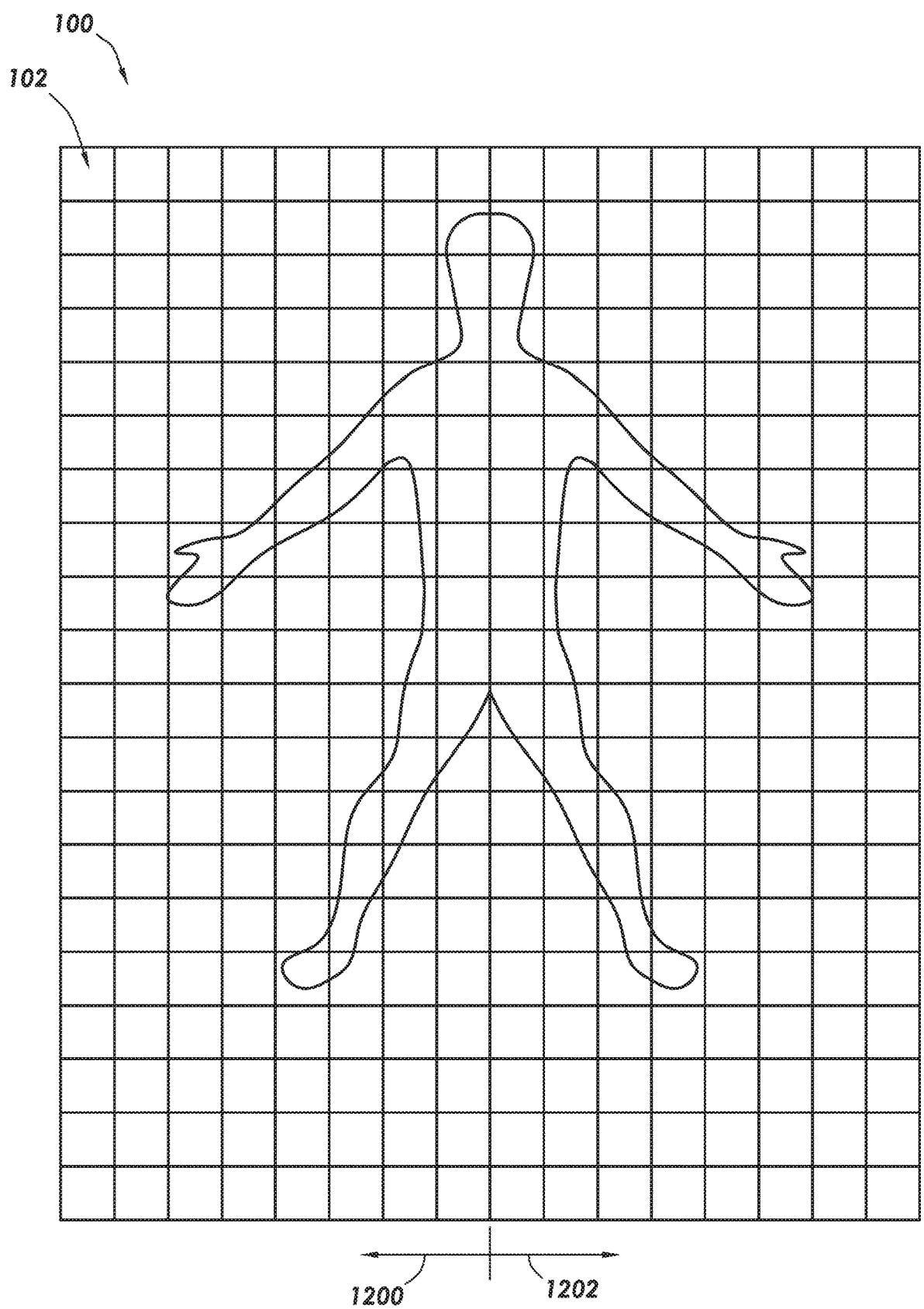
FIG. 12 shows an overhead view of the sleeping surface of an adjustable sleeping system with the user of FIG. 11 shown in shorthand notation, and in accordance with at least some embodiments.
Figure 13:
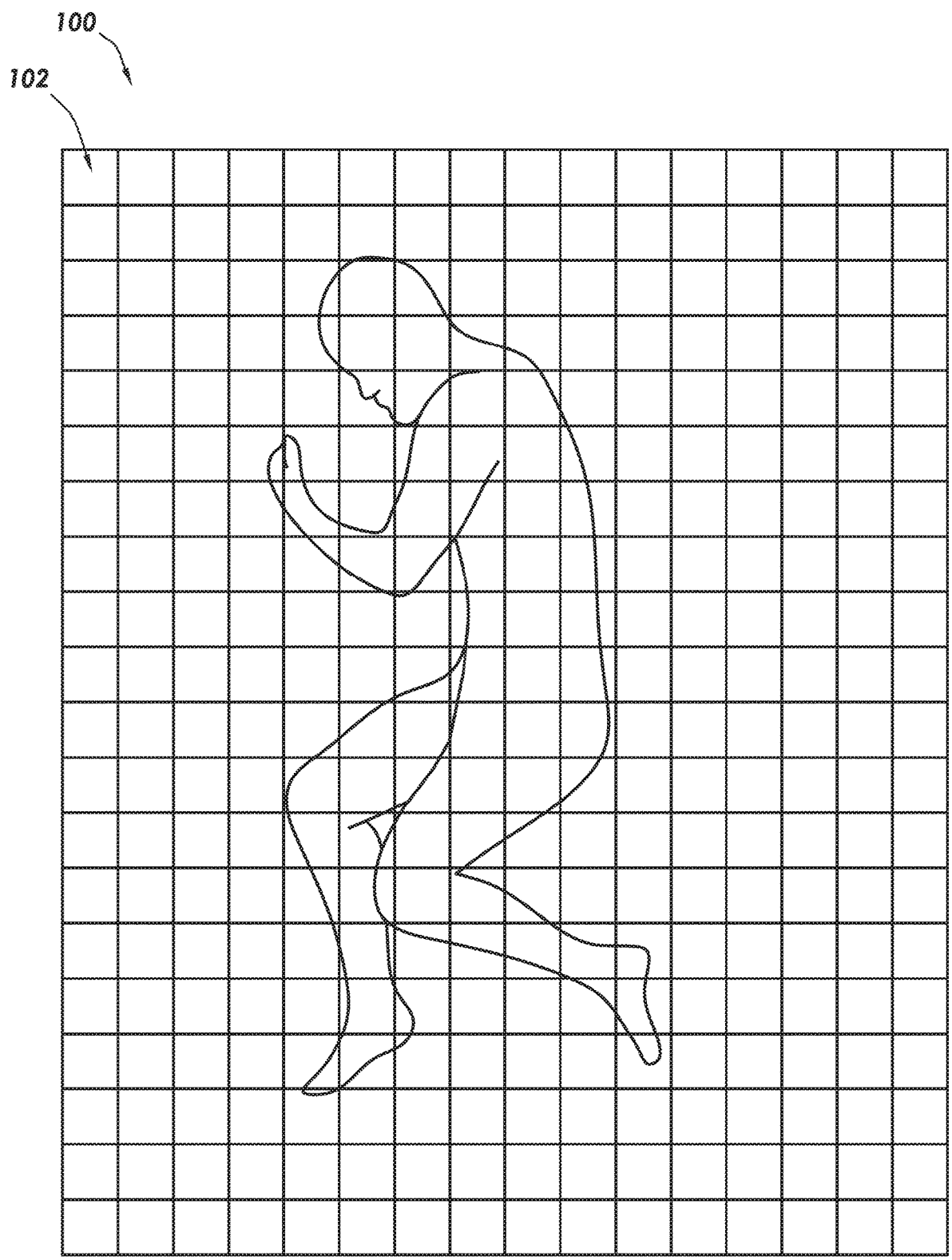
FIG. 13 shows an overhead view of the sleeping surface of an adjustable sleeping system with the user of FIG. 11 shown in shorthand notation, and in accordance with at least some embodiments.
Figure 14:
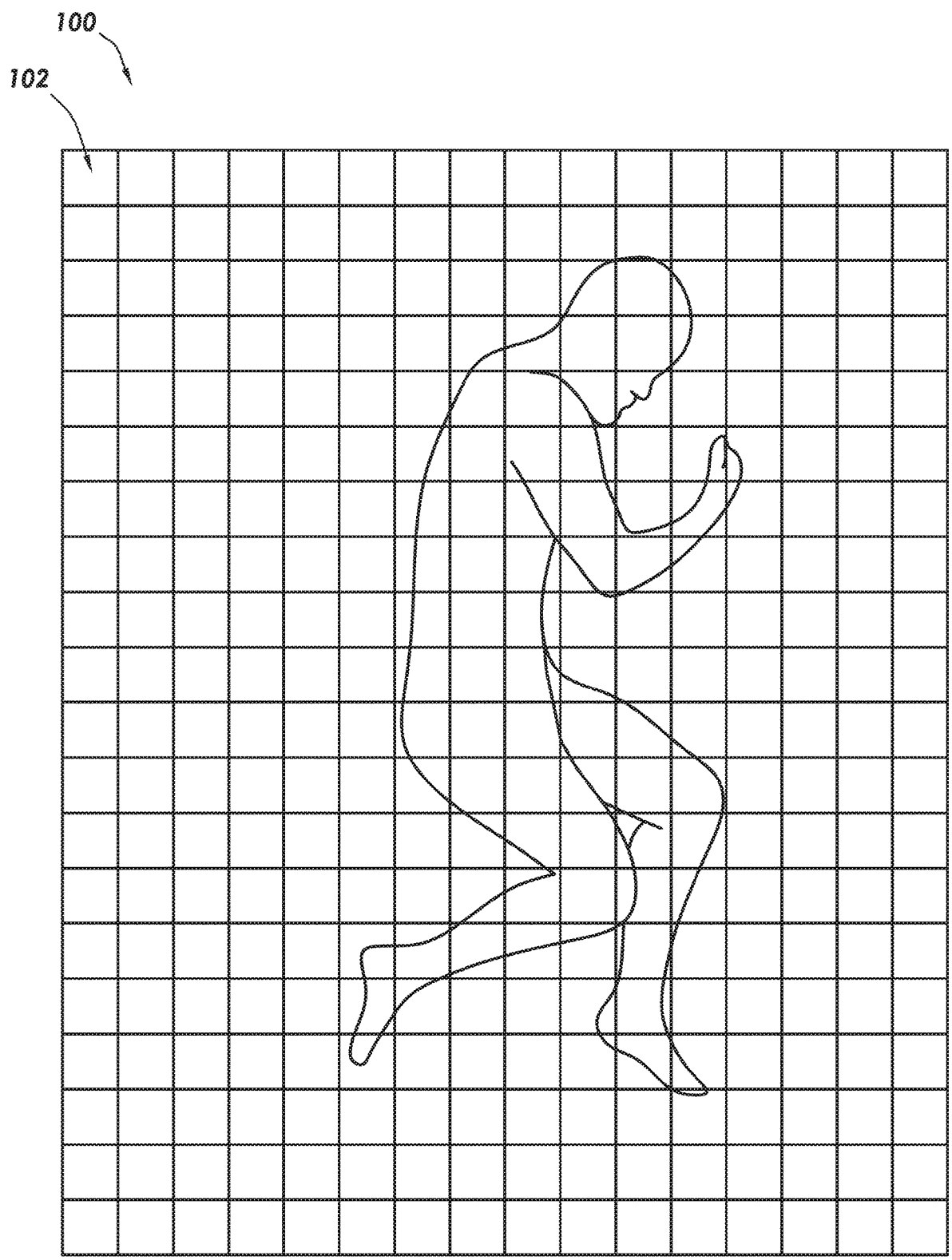
FIG. 14 shows an overhead view of the sleeping surface of an adjustable sleeping system with the user of FIG. 11 shown in shorthand notation, and in accordance with at least some embodiments.

FIG. 12 shows an overhead view of the sleeping surface 102 of an adjustable sleeping system 100 with the person of FIG. 11 shown in shorthand notation (e.g., the person's outline sketched out), and in accordance with at least some embodiments. FIG. 12 may thus represent the user residing face up, with the face up determination based on any available information, including initial force distribution. Face down will have similar shorthand notation, and thus face down is not specifically shown. FIG. 13 shows, in the shorthand notation, a user sleeping on the user's right side. FIG. 14 shows, in the shorthand notation, the user sleeping on the user's left side.

More particularly still, in example embodiments the bed controller 118 is configured to sense an actual body position of the person within the area. The actual body position may include: residing on the person's back (e.g., FIG. 12); residing on the person's right side (FIG. 13); residing on the person's left side (FIG. 14); and residing on the person's stomach. The determination may be made based on the values of force read from each of the plurality of adjustable spring assemblies 104 beneath the area. In some cases the bed controller 118 may be able to make the determinations based on instructions installed at the factory. In other cases, the bed controller 118 may implement a training phase where the person lays on the sleeping surface 102 in each of the positions and informs the bed controller 118 such that the bed controller 118 has basis functions for making the determination. In yet still other cases, the bed controller 118 may implement a neural network having input nodes and output nodes. The number of input nodes may correspond directly to the number of adjustable spring assemblies 104. The output nodes may be four output nodes, each output node producing a Boolean output to indicate the sleeping position of the user. Any non-zero number of intermediate layers (i.e., between the input nodes and output nodes), with any non-zero number nodes within each layer, may be used. In some cases, the neural network may be pre-trained before delivery to the end user. In other cases the training phase mentioned above may be used to train the neural network.

In accordance with example embodiments that implement a determination of body position, additional features may be implemented. In particular, example embodiments may implement a "follow me" feature and "cradle me" feature where one or more selected body portions are identified and special treatment provided. That is, in example methods, the person designates (e.g., by interaction with bed controller 118) one more portions to be selected body portions. Once designated, the bed controller 118 may determine a location of the selected body portion within the area based on the body position. As the person changes position, with each change of position the bed controller 118 may again determine the location of the selected body portion. If the selected body portion is in contact with the sleeping surface 102, the bed controller 118 may control force distribution by driving a first subset of the plurality of adjustable spring assemblies 104, the first subset beneath the selected body portion, to carry a different force than remaining adjustable spring assemblies. In some cases, the driving is to carry more force. Driving to carry more force may result in the selected body portion being held at a higher elevation relative to gravity than other, non-selected body portions. In yet still other cases, the driving is to carry less force.

Consider as an example of the "follow me" feature, that the person on the sleeping surface 102 has a right hip that is particularly sensitive to touch or pressure. Through interaction with the bed controller 118 (e.g., directly, or through an application running on the person's mobile computing device) the person could designate the right hip, and request that the force applied to the right hip be adjusted (e.g., reduced or increased). In the example method, first the sleeping position is determined, such as discussed above with respect to FIGS. 11-14. Once the sleeping position is determined, the example method implements the special treatment for the right hip, in this example, reducing force applied to the right hip. Consider that the person is initially face up as shown in FIG. 11. The bed controller 118 identifies the right hip for the current position of the person, and the bed controller 118 commands the spring assemblies 104 under the right hip to decrease force carried. In some cases, other spring assemblies in the vicinity of the example right hip will increase force to help hold the user relatively flat (e.g., attempting to keep the spine straight). As the user rolls to the right side, as shown in FIG. 13, again in the example method the bed controller 118 commands the spring assemblies 104 under the right hip to decrease force. And again, in some cases, other spring assemblies 104 in the vicinity of the example right hip increase force to help support the user in the desired configuration. If the user rolls to the left side, as shown in FIG. 14, no action is taken as the right hip is not in contact with the sleeping surface 102 of the adjustable sleeping system 100, but as soon the user returns to a position where the example right hip is in contact, the method continues.

Consider, as an example of the "cradle me" feature, that the user has a left knee or lower leg issue that is made better by having the left leg elevated. The person could thus designate the left leg through interaction with the bed controller 118 (e.g., directly, or through an application running on the person's mobile computing device), and request that the special treatment be holding the left leg higher than the hips and torso. In the example method, first the sleeping position is determined, such as discussed above with respect to FIGS. 11-14. Once the sleeping position is determined, the example method implements the special treatment for the left leg, in this example, increasing force applied to left leg, possibly while decreasing force to remaining locations where the body is present with the result being the left leg is held higher than the remaining body parts. Depending on the density of the spring assemblies implemented, the spring assemblies at the location of the left knee and lower leg may indeed implement force distribution that is trough-like, with higher forces at the "edges" of the leg, and lower forces in the center of the calf region, to not only hold the left leg higher but also tend to center and cradle the leg in the trough-like region.

In accordance with example embodiments that implement a determination of position of the person on the sleeping surface, another feature that may be implemented is a feature to cause or encourage the person to roll. In particular, these example methods comprise sensing (e.g., by the bed controller 118), an actual body position of the person within the area. The example method may comprise driving the plurality of adjustable spring assemblies to encourage a roll of the person from the actual body position to a second body position. Encouraging a roll may be from any actual body position to any suitable second body position. For example, encouraging a roll may include: driving the plurality of adjustable spring assemblies to encourage the roll of the person from the actual body position being laying on the person's back to the second body position being laying on the person's side; and driving the plurality of adjustable spring assemblies to encourage the roll of the person from the actual body position being laying on the person's side to the second body position being laying on the person's back.

The specification refers to "encourage" a roll for a couple of reasons. First, depending a host of factors (e.g., weight of the person, un-laden length of the main springs 320, total travel distance of the spring plates 318 along respective lead screws 316), it may not be possible to physically roll the person from position-to-position using only the adjustable spring assemblies 104. Second, a roll from one position to the next position may involve repositioning arms and/or legs relative to the person's torso, which may not be possible using only the adjustable spring assemblies 104. Thus, the example embodiments adjust some or all of the plurality of adjustable spring assemblies to encourage the roll with the goal of causing a brain arousal sufficient to have the person wake sufficiently to complete roll on their own.

Consider, as an example, a person sleeping face up (i.e., the person's back on the sleeping surface 102). Further consider that the person is experiencing sleep apnea in the form of snoring. The bed controller 118 may determine that the person is snoring. For example, vibrations associated with snoring may be sensed by the force sensor 502 (FIG. 5) in a subset of the plurality of the adjustable spring assemblies 104 (e.g., adjustable spring assemblies 104 beneath the head and/or chest of the person). In other cases, the bed controller 118 may sense the snoring by way of the microphone 818 (FIG. 8). In yet still other cases, a sleeping partner may interact with the bed controller 118 (e.g., directly, or through an application running on the person's mobile computing device) to inform the bed controller 118 of the issue. Regardless of how the bed controller 118 determines the person is snoring, in the example case the bed controller 118 may encourage a roll by driving a first subset of the plurality of adjustable spring assemblies 104 to carry less force, and driving a second subset of plurality of the adjustable spring assemblies 104 to carry more force.

Consider, as an even more specific example, the bed controller 118 encourages a roll from the person's back to the person's right side. In such a situation, and referring again to FIG. 12, the bed controller 118 may drive the first subset of the plurality of adjustable spring assemblies 104 to carry less force, the first subset being adjustable spring assemblies 104 in columns on the on right side of the person's body (the right side of the person shown by arrow 1200). In some cases, the bed controller 118 may drive first subset to carry a lower force, such as a minimum force (e.g., the springs plates 318 are driven to their zero position). Stated otherwise, the first subset of the adjustable spring assemblies 104 may be driven to a more plush position, such as the extra plush position. Moreover, the bed controller 118 may drive the second subset of the plurality of adjustable spring assemblies 104 to carry more force, the first subset being adjustable spring assemblies 104 in columns on the on left side of the person's body (the left side of the person shown by arrow 1202). In some cases, the bed controller 118 may drive the second subset to carry a higher force, such as a maximum force (e.g., the springs plates 318 are driven to their most distal position along their respective lead screws 316). Stated otherwise, the second subset of adjustable spring assemblies 104 may be driven to a more firm position, such as the extra firm position. In cases where the adjustable spring assemblies 104 have massage springs 600 (FIG. 6), the second subset of the adjustable spring assemblies 104 may be driven such that the massage springs 600 carry some or all the force of each adjustable spring assembly 104 of the second subset. Regardless of the precise nature of the driving of the first and second subsets of adjustable spring assemblies, the bed controller 118 encourages a roll from an actual body position being the person on their back to a second body position being the right side, in this example.

In accordance with example embodiments that implement a determination of body position, yet still further features may be implemented. In particular, example embodiments may implement a disembarkation feature. That is, in example methods sensing the body position may further comprise sensing that the person is positioned for disembarkation from the sleeping surface. That is, the bed controller 118 may determine, based on reading force values from the array of adjustable spring assemblies 104, that the person is positioned at the edge of the sleeping surface. Determining that the person is positioned at the edge of the sleeping surface for disembarkation may be distinguished from other positions both by force carried and size of the area. That is, when a person is laying on the sleeping surface 102, the person's weight is distributed over an area whose length and width is proportional to the size of the person. When positioned for disembarkation, by contrast, the person is likely sitting on the end of the bed with the legs and feet dangling off the bed (possibly with the feet resting on the floor). Regardless, once the bed controller 118 determines that the person is positioned for disembarkation, the example method comprises driving the plurality of adjustable spring assemblies to assist the disembarkation.

Driving to assist the disembarkation may take many forms. In cases where the sleeping surface 102 is closer to the floor than a length of a person's legs, driving the plurality of adjustable spring assemblies 104 to assist disembarkation may involve driving the plurality of adjustable spring assemblies to increase force carried by the plurality of adjustable spring assemblies 104. Increasing the force may raise the buttocks of the person relative to the floor to reduce the amount of leg extension needed to stand. Stated otherwise, these example embodiments make the edge of the sleeping surface 102 more firm (e.g., driving all the way to extra firm) to assist in disembarkation. Oppositely, in cases where the sleeping surface 102 is farther from the floor than the length of the person's legs, driving the plurality of adjustable spring assemblies to assist the disembarkation may involve driving the plurality of adjustable spring assemblies to decrease force carried by the plurality of adjustable spring assemblies 104. Decreasing the force may lower the buttocks of the person relative to the floor to reduce or eliminate the distance from the person's feet to the floor to reduce or eliminate the need to jump down to the floor. Stated otherwise, these example embodiments make the edge of the sleeping surface 102 softer (e.g., extra plush) to assist in disembarkation.

Another example feature that may be implemented in systems where a determination of body position is implemented is a maternity feature. In particular, when the pregnant person is on her left side or right side, the adjustable spring assemblies 104 under her belly may provide additional support. Moreover, once the adjustable sleeping system 100 is aware of the pregnancy, the systems and methods may track growth and weight change.

Another example feature that may be implemented in systems where a determination of body position is implemented is spinal alignment, and in some cases intentional spinal misalignment. In particular, since the spring constants for the main springs 320 are known, and the force carried by each main spring 320 is measured in many cases, it is possible to calculate the location of the upper or second end 324 (FIG. 3) of each main spring 320. Thus, once a sleeping position is determined, it is possible to implement any desired alignment, or misalignment, of the spine of the user.

In addition to, or in place of, the force control features discussed above, example embodiments may also implement a massage feature or massage function. In particular, some example embodiments massage a person residing on the sleeping surface 102 of the adjustable sleeping system 100. More particularly, example methods comprise sensing the area of the sleeping surface 102 upon which the person resides as discussed above. Massaging may comprise driving the plurality of adjustable spring assemblies beneath the area.

The massage function may take several forms. For example, the massage function may be at a single location on the sleeping surface 102 (e.g., implemented by a single adjustable spring assembly 104). With respect to the single location, in example methods the person designates (e.g., by interaction with bed controller 118) the single location. Once designated, the bed controller 118 implements the massage function using the adjustable spring assembly 104 at the single location. In other cases, the massage function may be implemented within a designated area less than the entire area upon which the person resides. With respect to a designated area, in example methods, the person designates (e.g., by interaction with bed controller 118) the designated area. Once designated, the bed controller 118 implements a massage function within the designated area. Further still, the massage function may be with respect to a particular body portion less than the entire body. With respect to a particular body portion, in example methods, the person designates (e.g., by interaction with bed controller 118) the selected body portion. Once designated, the bed controller 118 may determine a location of the selected body portion within the area based on the body position, and the massage function may be implemented only with respect to that selected body portion (e.g., shoulders, neck, or lower back). Further still, the massage function may be with respect the entire area within which the person resides.

In situations where the massage function is implemented within an area larger than a single adjustable spring assembly 104, the massage function may take many forms. For example, within the area the massage function may be implemented in a random or pseudo-random pattern. In another example, within the area the massage function may be implemented as a predetermined pattern of one or more spring assemblies implementing increased force. The predetermined pattern may be any suitable pattern or repeating pattern. As yet another example, within the area the massage function may be implemented as travelling wave fronts of increased force, the travelling wave fronts moving in any suitable direction.

Figure 15:
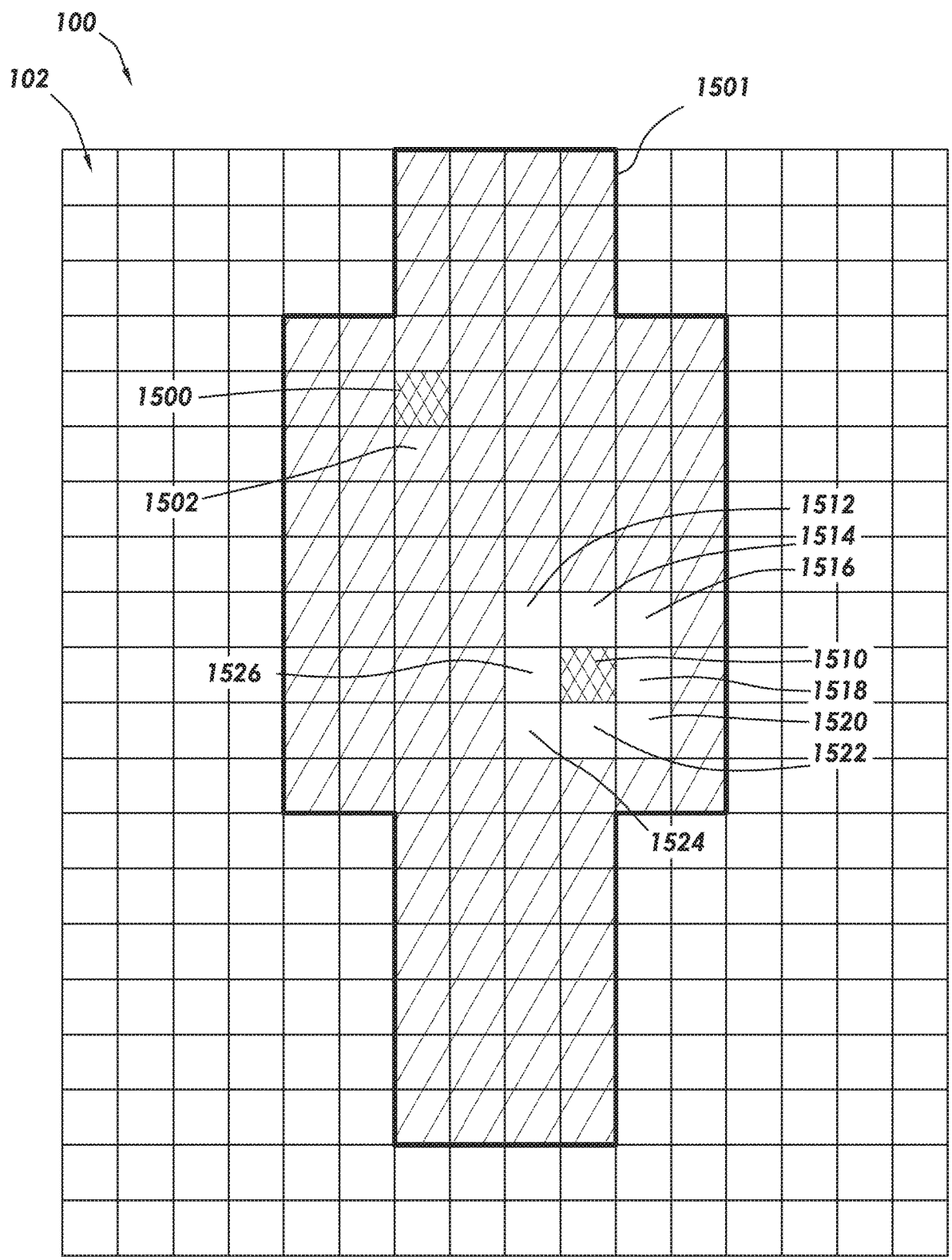
FIG. 15 shows an overhead view of the sleeping surface of an adjustable sleeping system, in accordance with at least some embodiments.

FIG. 15 shows an overhead view of the sleeping surface 102 of an adjustable sleeping system 100 in order to discuss the example massage function in greater detail, and in accordance with at least some embodiments. In particular, as before the example sleeping surface 102 is conceptually, though not necessarily physically, divided into a grid with each square in the grid representing the location of an adjustable spring assembly 104. The size of the squares representing the locations of the adjustable spring assemblies 104 is exaggerated for purposes of clarity. FIG. 15 shows an example area 1501 within which a person laying in a face-up or face-down position with arms at the person's sides, and with adjustable spring assemblies carrying load shown with shading. The shading is mostly uniform in FIG. 15 so as not to unduly complicate the figure, with two example non-uniform loadings discussed in greater detail below. However, the force distribution would again track the contours and weight distribution of the user (prior to force normalization, if implemented).

In some example cases, massaging the person may comprise driving a first adjustable spring assembly 104 to carry more weight or force than a nearest neighbor adjustable spring assembly 104. For example, in FIG. 15 the adjustable spring assembly beneath location 1500 is driven to carry more weight or force, as shown by the denser surface shading compared to an example nearest neighbor location 1502 (e.g., a nearest neighbor being an abutting location or contiguous location in any direction). Thus, location 1500 is an example of a massage function at a single location, or a single point of massage within designated area (e.g., beneath a selected body portion). In some cases, the driving to carry more force may comprise driving the first adjustable spring assembly to increase compression of the main spring by at least one inch, and in a particular case driving the first adjustable spring assembly 104 to increase compression by at least three inches. The massage function may then further comprise driving the first adjustable spring assembly 104 to carry an original force (not specifically shown in FIG. 15). Using adjustable spring assemblies having only the main spring 320 (FIG. 3), or during periods of time before the massage spring 600 (FIG. 6) engages, the increased force concentration on the body of the person may be within an area of about nine square inches (e.g., three inches by three inches). The experience may be heighten in cases where the adjustable spring assemblies 104 include the massage springs 600. When the massage spring 600 engages, the force concentration on the body may be within a smaller area being about four square inches (e.g., two inches by two inches). The experience may be further heighten in cases where the adjustable spring assemblies 104 have a smaller diameter main spring 316. With a smaller diameter main spring 316, the force concentration on the body may be within a smaller area still (e.g., about one square inch for a one inch diameter main spring 316). The driving of the first adjustable spring assembly 104 to carry more force, and then driving the first adjustable spring assembly 104 to again carry less force (e.g., back to the original force), may mimic a massage function of a thumb pressing on a sore muscle (e.g., on a knot in a muscle), or an elbow pressing on a sore muscle in a deep tissue massage.

In example cases, each adjustable spring assembly 104 is designed and constructed to drive its respective spring plate 318 (FIG. 3) from the extra plush position to the extra firm position in about four seconds. Stated otherwise, in example cases each adjustable spring assembly 104 is designed and constructed to drive its respective spring plate 318 (FIG. 3) from a position closest to the top plate 404 (FIG. 6) to a position farthest from the top plate 404 in about four seconds. A complete cycle of an example massage function based on a full scale travel and back of the spring plate 318 along the lead screw 316 may take about eight seconds. However, depending on the initial setting for firmness and/or the any adjustments made to implement force control, the driving may be from an intermediate position to the position farthest from the top plate 404 and back to the intermediate position, and thus in other cases a complete cycle of a massage function may take about four seconds.

Still referring to FIG. 15, as another example of the massage function consider that the adjustable spring assembly beneath location 1510 is driven to carry more weight or force, and that at least one nearest neighbor adjustable spring assembly is driven to carry less weight or force. Thus, location 1510 is an example of a massage function at a single location, or a single point of massage within designated area (e.g., beneath a selected body portion). In the example of FIG. 15, the abutting and contiguous nearest neighbor adjustable spring assemblies beneath locations 1512, 1514, 1516, 1518, 1520, 1522, 1524, and 1526 are driven to carry less weight or force to heighten the experience with respect to the adjustable spring assembly beneath location 1510 carrying more weight or force. In some cases, the driving is simultaneous (e.g., location 1510 driven to carry more force simultaneous the remaining contiguous and abutting locations driven to carry less force). In other cases, the contiguous and abutting locations may be driven initially to carry less force, and remain at the lower force settings as the main location 1510 cycles between higher force and less force. In these example cases, the massage function may be implemented as a change in relative compression of the main spring for the adjustable spring assembly at the main location 1510 relative to compression of a main spring of a nearest neighbor adjustable spring assembly (e.g., location 1512). For example, the driving to carry more force may comprise driving the adjustable spring assembly beneath the main location 1510 to increase relative compression with respect to a nearest neighbor adjustable spring assembly by at least one inch (e.g., the main spring beneath location 1510 increased by 0.5 inch while the main spring beneath location 1512 decreased by 0.5 inch), and in a particular case increasing the relative compression by two inches or more.

With respect to the area upon which a person resides, the massage function may also take many forms. For example, once the area upon which the person resides is determined (in any suitable form), driving the plurality of adjustable spring assemblies may comprise driving in a random pattern within the area. In other cases, the massage function may comprise receiving, by the bed controller 118, a designation of a selected area, the selected area less than the entire area over which person resides. With the selected area, the bed controller 118 may implement a massage function by driving the plurality of adjustable spring assemblies beneath the selected area (e.g., in a random pattern, a predefined pattern, or as traveling wave fronts of increased force) and refraining from driving adjustable spring assemblies beneath non-selected areas. In other cases, the massage function may comprise receiving, by the bed controller 118, a designation of a selected body portion of the person, the selected body portion being less than all the body portions of the person. With the selected body portion, the bed controller 118 may determine a location of the selected body portion on the sleeping surface, and then implement a massage function by driving the plurality of adjustable spring assemblies beneath the selected body portion (e.g., in a random pattern, a predefined pattern, or as traveling wave fronts of increased force) and refraining from driving adjustable spring assemblies beneath non-selected body portions and outside the area. If the person changes body position and the selected body portion is in contact with the sleeping surface 102, the bed controller 118 may determine the new location of the selected body portion, and continue the massage function at the new location. The specification now turns to a more detailed description of the traveling wave fronts of increased force.

Figure 16:
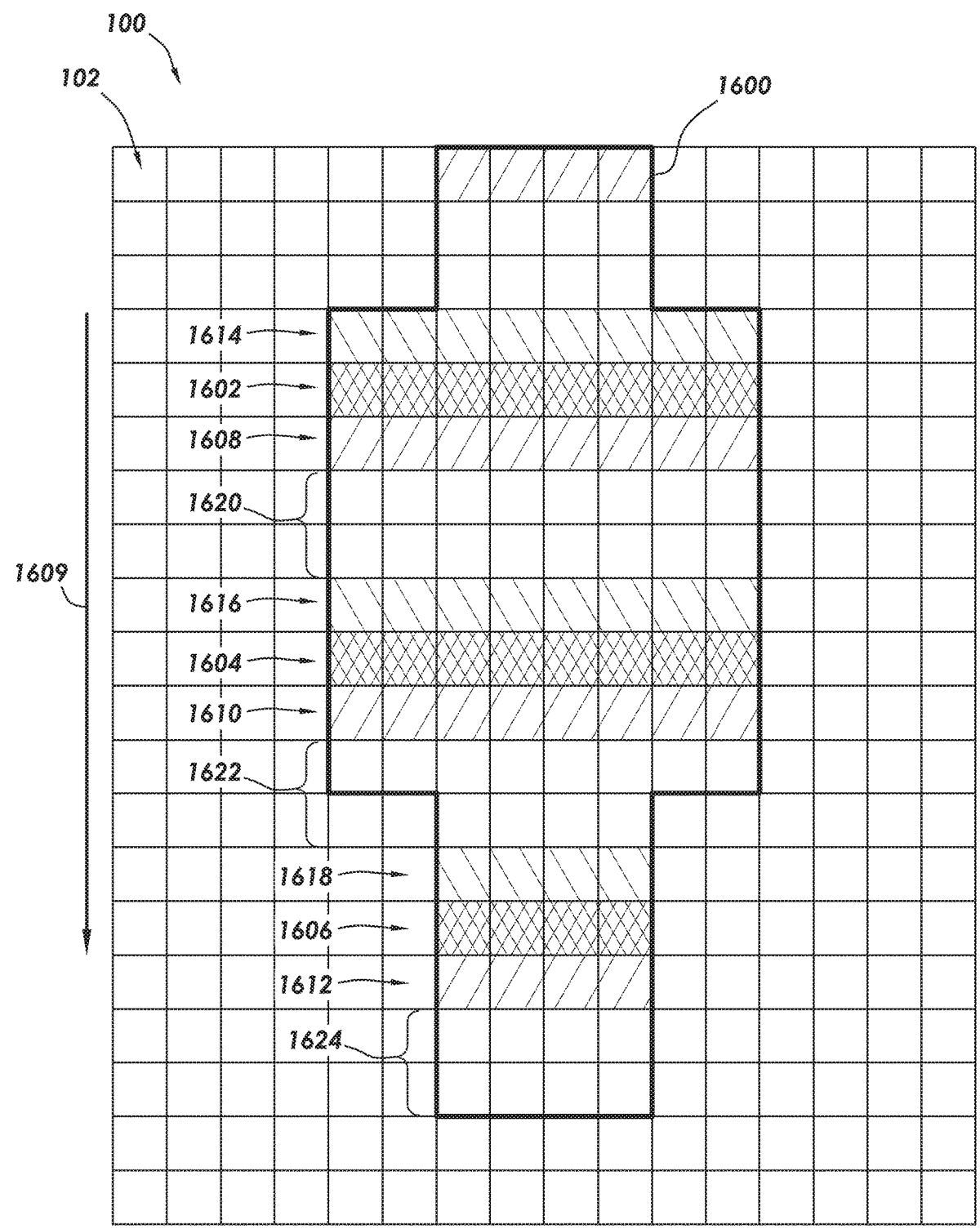
FIG. 16 shows an overhead view of the sleeping surface of an adjustable sleeping system, in accordance with at least some embodiments.

FIG. 16 shows an overhead view of the sleeping surface 102 of an adjustable sleeping system 100 in order to further discuss the massage function, and in accordance with at least some embodiments. As before the example sleeping surface 102 is conceptually, though not necessarily physically, divided into a grid with each square in the grid representing the location of an adjustable spring assembly 104. FIG. 16 shows an area 1600 within which a person is laying in a face-up or face-down position with arms at the person's sides. Further, FIG. 16 shows a snapshot in time of a massage function comprising travelling wave fronts of increased force. In particular, FIG. 16 shows that the massage function in example embodiments is not limited to single adjustable spring assemblies being driven to carry increased force to implement the massage function; rather, in other cases the massage function may involve subsets of the plurality of adjustable spring assemblies 104 beneath the area working together to implement example massage function. FIG. 16 shows three example wave fronts of increased force, being wave fronts 1602, 1604, and 1606. The wave fronts may travel in any direction relative to the sleeping surface 102, such as from the person's head to the person's feet, from the person's feet to the person's head, and across the body in either direction (the across-body not specifically shown in FIG. 16), to name a few examples. For purposes of explanation, however, consider that the wave fronts 1602, 1604, and 1606 are traveling toward the foot of the bed, as shown by arrow 1609.

Referring to wave front 1602 as representative, a subset of adjustable spring assemblies 104 along a width (e.g., along a row) of the wave front are driven to carry increased force. In some cases, and as shown, the wave "crest" has a width (e.g., along the columns) of a single adjustable spring assembly. However, in other cases the wave "crest" may comprise one or more adjustable spring assemblies, and in a particular case between and including two to six adjustable spring assemblies. In some cases, adjustable spring assemblies on the leading edge of the wave front are being driven to carry more force, and the adjustable spring assemblies on the trailing edge of the wave front are being driven to carry less force. In the example case of the wave fronts travelling toward the foot of the bed, the adjustable spring assemblies on the leading edge of each wave front, for example leading edges 1608, 1610, and 1612, at the snapshot in time, are being driven to carry more force. At the same snapshot in time, the adjustable spring assemblies on the trailing edge, for example trailing edges 1614, 1616, and 1618, are being driven to carry less force. In some cases, the adjustable spring assemblies in the troughs between wave crests (e.g., troughs 1620, 1622, and 1624) are driven to carry lower force, and in some cases driven to carry the least amount of force the adjustable spring assemblies can carry. The plurality of adjustable spring assemblies are driven such that the wave front of increased force moves along the area 1600. Thus, adjustable spring assemblies forming a crest at one moment in time will, a few second later and depending on propagation speed of the wave front, be driven to carry less force (e.g., a trough ahead or behind the crest) as the wave front moves along the area of the sleeping surface 102.

Considering, as an example, a situation where each of the plurality of adjustable spring assemblies 104 implementing the travelling wave front massage function is driven from the extra plush to extra firm and back in eight seconds. It follows that a wave crest, and thus the wave front, could move at a speed about four adjustable spring assemblies in eight seconds. If the wave front is aligned with the rows of the example adjustable sleeping system 100 (FIG. 1) as shown in FIG. 16, and if there are 24 rows that make up the adjustable sleeping system 100, then a wave front could travel the length of the bed in about 16 seconds. If each of the plurality of adjustable spring assemblies 104 implementing the travelling wave front massage function is driven from an intermediate position (e.g., medium firm) to extra firm and back in four seconds, the wave front could move at a speed about two adjustable spring assemblies in four seconds. If the wave front is aligned with the rows of the example adjustable sleeping system 100 (FIG. 1) as shown in FIG. 16, and if there are 24 rows that make up the adjustable sleeping system 100, then a wave front could travel the length of the bed in this example in about eight seconds.

The distance between the crests of the wave fronts can have any separation distance. Moreover, the speed at which the wave front travels is not limited to the fastest speeds, and the speeds include travel times along the length of the adjustable sleeping system 100 between and including 8 to 60 seconds, in a particular case between and including 10 and 20 seconds. The wave fronts need not be aligned with the rows, and in fact need not be straight or extend fully across the person. The bed controller 118 may receive a designation of any or all the parameters associated with the wave fronts (e.g., wave front shape, direction of travel, speed of travel, distance between wave fronts, force carried along each crest), and command the control PCBs 436 to drive their respective motors 312 to implement the traveling wave fronts. Moreover, the traveling wave fronts are not mutually exclusive with other force control functions, and thus may be implemented in addition to any or all the functions discussed above.

In addition to the various force control functions, the example systems may gather and provide information to the user. For example, in some example cases the adjustable sleeping system 100 may be able to measure the absolute weight of a person, and thus the adjustable sleeping system 100 can track change of weight over time, such as overnight or over the course of days or weeks. In other cases, while the adjustable sleeping system 100 may not be able to measure accurately the absolute weight of a person, the adjustable sleeping system 100 can track change of weight over time, such as overnight or over the course of days or weeks. Changes in overnight weight loss may be indicative of medical conditions, such as conditions that result in night sweats. The example information may be conveyed to the user in any suitable form, such as the bed controller 118 communicating to the user's mobile computing device using any suitable short-range communication protocol, such as Bluetooth.

Additional information that may be determined includes the adjustable sleeping system 100 generating a value indicative of quality of sleep. Quality of sleep can be affected by many factors, both physiological and environmental. Because each adjustable spring assembly 104 separately and independently measures weight or force, the adjustable sleeping system 100 in example embodiments senses movements of the user that are indicative of poor sleep quality. For example, if the user has restless leg syndrome, the adjustable sleeping system 100 may sense leg movement throughout the night as variances in measured force. When restless leg syndrome is detected, the adjustable sleeping system 100 may inform the user, and even lower the value indicative of quality of sleep based on the determination.

As yet another example of information that may be determined, every time a user rolls over and/or changes position, the movement is indicative of a brain arousal that adversely affects quality of sleep. Thus, the adjustable sleeping system 100 in example embodiments senses movements associated with the person tossing and turning, and how frequently the position changes are made. The adjustable sleeping system may thus lower the value indicative of sleep quality as the number and/or frequency of the position changes increases.

As yet another example of information that may be determined, every instance of a person rising and leaving the adjustable sleeping system 100 during the night is indicative of a waking event that adversely affects quality of sleep. Thus, the adjustable sleeping system 100 in example embodiments sense each disembarkation. The adjustable sleeping system may thus lower the value indicative of sleep quality based on the number and/or frequency of disembarkation events throughout the night.

In yet still other cases the example system may sense breakthrough breaths associated with obstructive or central sleep apnea. In cases of sleep apnea, the user stops breathing for a period of time, which can result in dangerously low blood oxygen levels. If the force sensor 502 (FIG. 5) of each adjustable spring assembly 104 is sensitive enough, force distribution changes associated with respiration may be sensed as force oscillations within frequency ranges associated with breathing. When breathing stops, the value indicative of sleep quality may be adjusted downward. Regardless of the type of apnea, when breathing resumes the first breath is termed a breakthrough breath, and in most cases results in rapid and deep inhalation. Thus, even if the adjustable spring assemblies 104 are not sensitive enough to sense breathing, breakthrough breaths may be sensed. Again, each time a breakthrough breath is sensed, the value indicative of sleep quality may be adjusted downward. Obstructive apnea is in some cases position dependent, and thus when the example adjustable sleeping system 100 senses breakthrough breaths, in systems where the body position of the person is detected, the example adjustable sleeping system 100 may proactively encourage a roll as discussed above.

In a function related to the massage function, the adjustable spring assemblies 104 may be used to rock the person back and forth about the centerline of the body, such as the centerline parallel to the spine. In particular, the rocking may be implemented by wave fronts of increased force propagation across the body of the person (e.g., propagating parallel to the width W of the adjustable sleeping system), with the distance between crests being greater than a width of the person's body. In yet another related function, the massage function may implement a wakeup function, where the massage function is used to wake the user, possibly integrated with music, and more particularly synchronized with the beat of the music. In some cases, the beat or timing of the music may be mimicked by the massage function; however, given the speed of movement of the spring plates 318 (FIG. 3), the beat alignment may, for example, be on every fourth or eighth beat of the music.

The above discussion is meant to be illustrative of the principles and various embodiments of the present invention. Numerous variations and modifications will become apparent to those skilled in the art once the above disclosure is fully appreciated. For example, the control PCBs 436 are shown to be daisy-chained together along a row for communicative purposes; however, in other cases the bed controller 118 may have a separate communication channel to each control PCB 436. As another example, an overall bed may be conceptually (though not necessarily physically) divided such that two users could individually control their respective sides, including individual control of firmness, message, force neutralization, spine alignment and/or any other function implemented by the bed system. It is intended that the following claims be interpreted to embrace all such variations and modifications.

What is claimed is:

1. A method of operating a sleeping system, the method comprising:
    massaging a person residing on a sleeping surface of the sleeping system, the sleeping system comprising a plurality of adjustable spring assemblies that are part of an array of adjustable spring assemblies arranged such that a top of each adjustable spring assembly defines an upper surface parallel to the sleeping surface, the massaging comprising driving the plurality of adjustable spring assemblies so as to effectuate a travelling wave front across the sleeping surface, the travelling wave front being driven from an initial position to an end position on the sleeping surface at a speed that is based on an initial vertical position of each of the plurality of adjustable spring assemblies and a quantity of the plurality of adjustable spring assemblies.

2. The method of claim 1 further comprising:
    sensing an area of the sleeping surface upon which the person resides, the sensing configured to be achieved by a bed controller communicatively coupled to the array of adjustable spring assemblies; and
    wherein driving the plurality of adjustable spring assemblies further comprises driving the plurality of adjustable spring assemblies being the adjustable spring assemblies beneath the area.

3. The method of claim 1 further comprising:
    sensing, by a bed controller, an area of the sleeping surface upon which the person resides by reading a force value from the array of adjustable spring assemblies, each adjustable spring assembly comprising a force sensor configured to measure an amount of force carried by the respective adjustable spring assembly; and
    wherein driving the plurality of adjustable spring assemblies further comprises driving the plurality of adjustable spring assemblies being the adjustable spring assemblies beneath the area.

4. The method of claim 1, wherein driving the plurality of adjustable spring assemblies further comprises driving the plurality of adjustable spring assemblies in a predetermined pattern.

5. The method of claim 4, wherein the predetermined pattern is based at least on a parameter associated with at least one of a shape of the wave front, the speed of the wave front, a direction of travel and distance between wave fronts.

6. The method of claim 1, wherein the travelling wave front comprises a wave front with increased force in a direction of travel relative to the person on the sleeping surface.

7. The method of claim 1 further comprising:
    receiving, by a bed controller, an indication of a selected body portion of the person, the selected body portion being less than all body portions of the person;
    sensing, by a bed controller, an area of the sleeping surface upon which the person resides;
    determining a location of the selected body portion on the sleeping surface;
    and wherein driving the plurality of adjustable spring assemblies further comprises driving the plurality of adjustable spring assemblies beneath the selected body portion and refraining from driving adjustable spring assemblies beneath non-selected body portions.

8. The method of claim 1, wherein driving the plurality of adjustable spring assemblies further comprises driving a first adjustable spring assembly to carry more force than a nearest neighbor adjustable spring assembly.

9. The method of claim 8, wherein driving the first adjustable spring assembly further comprises increasing compression of a main spring of the first adjustable spring assembly by at least one inch.

10. The method of claim 8 further comprising:
    driving the nearest neighbor adjustable spring assembly to carry less force.

11. The method of claim 1, wherein driving the plurality of adjustable spring assemblies further comprises driving the plurality of adjustable spring assemblies with each adjustable spring assembly comprising a massage spring concentrically disposed within a main spring, and the driving such that each massage spring carries more force than the respective main spring.

12. The method of claim 1, wherein the array of adjustable spring assemblies further comprises at least one selected from a group comprising:
    100 or greater adjustable spring assemblies; 100 or greater adjustable spring assemblies arranged as a cot size bed; 120 or greater adjustable spring assemblies arranged as a twin size bed; 200 or greater adjustable spring assemblies arranged as a twin size bed; 200 or greater adjustable spring assemblies arranged as a queen size bed; 400 or greater adjustable spring assemblies arranged as a queen size bed; 200 or greater adjustable spring assemblies arranged as a king size bed; and 400 or greater adjustable spring assemblies arranged as a king size bed.

13. An adjustable sleeping system comprising:
    an array of adjustable spring assemblies arranged such that a top of each adjustable spring assembly defines an upper surface parallel to a sleeping surface of the adjustable sleeping system, each adjustable spring assembly having a main spring with an un-laden compression that is adjustable;
    and a bed controller communicatively coupled to each of the adjustable spring assemblies, the bed controller configured to drive a plurality of the adjustable spring assemblies to massage a person residing on the adjustable sleeping system so as to effectuate a travelling wave front across the sleeping surface, the travelling wave front being driven from an initial position to an end position on the sleeping surface at a speed that is based on an initial vertical position of each of the plurality of adjustable spring assemblies and a quantity of the plurality of adjustable spring assemblies.

14. The adjustable sleeping system of claim 13 wherein, the bed controller is configured to sense an area of the sleeping surface upon which the person resides; and wherein when the bed controller drives the plurality of the adjustable spring assemblies, the bed controller is further configured to drive the plurality of adjustable spring assemblies beneath the area.

15. The adjustable sleeping system of claim 13 wherein, each adjustable spring assembly further comprises a force sensor associated with the main spring, the force sensor configured to measure an amount of force carried by the respective adjustable spring assembly, and the bed controller configured to read a value indicative of the amount of force carried from each adjustable spring assembly;
the bed controller configured to sense, by way of the force sensor of each adjustable spring assembly, an area of the sleeping surface upon which the person resides;
and wherein when the bed controller drives the plurality of the adjustable spring assemblies, the bed controller is further configured to drive the plurality of adjustable spring assemblies being the adjustable spring assemblies beneath the area.

16. The adjustable sleeping system of claim 13, wherein the travelling wave front comprises a wave front with increased force in a direction of travel relative to the person.

17. The adjustable sleeping system of claim 13, wherein when the bed controller drives the plurality of the adjustable spring assemblies, the bed controller is further configured to drive the plurality of the adjustable spring assemblies in a predetermined pattern.

18. The adjustable sleeping system of claim 17, wherein the predetermined pattern is based at least on a parameter associated with at least one of a shape of the wave front, the speed of the wave front, a direction of travel and distance between wave fronts.

19. The adjustable sleeping system of claim 13 wherein, the bed controller is configured to receive an indication a selected body portion of the person, the selected body portion being less than all the body portions of the person;
and the bed controller configured to sense an area of the sleeping surface upon which the person resides, and configured to determine a location of the selected body portion within the area, wherein when the bed controller drives the plurality of the adjustable spring assemblies, the bed controller is further configured to drive the plurality of adjustable spring assemblies beneath the selected body portion and configured to refrain from driving adjustable spring assemblies beneath non-selected body portions.

20. The adjustable sleeping system of claim 13, wherein when the bed controller drives the plurality of adjustable spring assemblies to massage the person, the bed controller is configured to drive a first adjustable spring assembly to carry more force than a nearest neighbor adjustable spring assembly.

21. The adjustable sleeping system of claim 20, wherein when the bed controller drives the first adjustable spring assembly, the bed controller is configured to increase compression of the main spring of the first adjustable spring assembly by at least one inch.

22. The adjustable sleeping system of claim 20, wherein the bed controller is further configured to drive the nearest neighbor adjustable spring assembly to carry less force.

23. The adjustable sleeping system of claim 13 wherein, each adjustable spring assembly further comprises a massage member concentrically disposed within the main spring of each adjustable spring assembly, wherein when the bed controller drives the plurality of the adjustable spring assemblies, the bed controller is further configured to drive the plurality of adjustable spring assemblies such that the respective massage members carry at least some of a force carried by each of the plurality of adjustable spring assemblies.

24. The adjustable sleeping system of claim 23, wherein each massage member is a massage spring with a spring constant higher than the main spring within which the massage spring is concentrically disposed.

25. The adjustable sleeping system of claim 13, wherein the adjustable spring assemblies further comprise at least one selected from a group comprising:
100 or greater adjustable spring assemblies; 100 or greater adjustable spring assemblies arranged as a cot size bed; 120 or greater adjustable spring assemblies arranged as a twin size bed; 200 or greater adjustable spring assemblies arranged as a twin size bed; 200 or greater adjustable spring assemblies arranged as a queen size bed; 400 or greater adjustable spring assemblies arranged as a queen size bed; 200 or greater adjustable spring assemblies arranged as a king size bed; and 400 or greater adjustable spring assemblies arranged as a king size bed.

* * * * *